(12) United States Patent
Hattori et al.

(10) Patent No.: US 9,216,995 B2
(45) Date of Patent: Dec. 22, 2015

(54) PYRIDONE DERIVATIVE HAVING INTEGRASE INHIBITORY ACTIVITY

(75) Inventors: Kazunari Hattori, Osaka (JP); Kenji Tomita, Osaka (JP)

(73) Assignee: SHIONOGI & CO., LTD., Osaka-Shi, Osaka (JP)

( * ) Notice: Subject to any disclaimer, the term of this patent is extended or adjusted under 35 U.S.C. 154(b) by 199 days.

(21) Appl. No.: 13/639,454

(22) PCT Filed: Apr. 11, 2011

(86) PCT No.: PCT/JP2011/002139
§ 371 (c)(1),
(2), (4) Date: Dec. 21, 2012

(87) PCT Pub. No.: WO2011/129095
PCT Pub. Date: Oct. 20, 2011

(65) Prior Publication Data
US 2013/0096109 A1    Apr. 18, 2013

(30) Foreign Application Priority Data

Apr. 12, 2010    (JP) .................................. 2010-091387

(51) Int. Cl.
| | | |
|---|---|---|
| *C07D 498/14* | (2006.01) | |
| *C07D 519/00* | (2006.01) | |
| *C07D 487/04* | (2006.01) | |
| *C07D 498/04* | (2006.01) | |
| *C07D 471/04* | (2006.01) | |

(52) U.S. Cl.
CPC ............ *C07D 498/14* (2013.01); *C07D 471/04* (2013.01); *C07D 487/04* (2013.01); *C07D 498/04* (2013.01); *C07D 519/00* (2013.01)

(58) Field of Classification Search
CPC .................................................... C07D 498/14
See application file for complete search history.

(56) References Cited

U.S. PATENT DOCUMENTS

| 7,211,572 B2 | 5/2007 | Miyazaki et al. |
|---|---|---|
| 7,550,463 B2 | 6/2009 | Yoshida |
| 2004/0229909 A1 | 11/2004 | Kiyama et al. |
| 2005/0054645 A1 | 3/2005 | Miyazaki et al. |
| 2006/0052361 A1 | 3/2006 | Miyazaki et al. |
| 2007/0249687 A1 | 10/2007 | Yoshida |
| 2008/0161271 A1 | 7/2008 | Yoshida et al. |
| 2008/0161311 A1* | 7/2008 | Miyazaki et al. ............. 514/248 |
| 2009/0143356 A1 | 6/2009 | Yoshida et al. |
| 2009/0318421 A1 | 12/2009 | Johns et al. |
| 2012/0115875 A1 | 5/2012 | Johns et al. |

FOREIGN PATENT DOCUMENTS

| EP | 1541558 A1 | 6/2005 |
|---|---|---|
| EP | 1544199 A1 | 6/2005 |
| EP | 1790638 A1 | 5/2007 |
| EP | 1874117 A1 | 1/2008 |
| EP | 1950212 A1 | 7/2008 |
| EP | 1544199 B1 | 10/2008 |
| EP | 2042502 A1 | 4/2009 |
| JP | H02-096506 | 4/1990 |
| JP | H02-108668 | 4/1990 |
| JP | H02-108683 | 4/1990 |
| JP | 2004-244320 A | 9/2004 |
| JP | 3814631 B2 | 8/2006 |
| JP | 2006-232849 A | 9/2006 |
| JP | 2008-540343 A | 11/2008 |
| JP | 2009-079058 A | 4/2009 |
| JP | 4295353 B2 | 7/2009 |
| WO | WO 03/016275 A1 | 2/2003 |
| WO | WO 03/035076 A1 | 5/2003 |
| WO | WO 2004/004657 A2 | 1/2004 |
| WO | WO 2004/024693 A1 | 3/2004 |
| WO | WO 2005/016927 A1 | 2/2005 |
| WO | WO 2006/030807 A1 | 3/2006 |
| WO | WO 2006/116764 A1 | 11/2006 |
| WO | WO 2007/049675 A1 | 5/2007 |
| WO | WO 2010/011812 A1 | 1/2010 |
| WO | WO 2010/011819 A1 | 1/2010 |

* cited by examiner

*Primary Examiner* — Paul Zarek
(74) *Attorney, Agent, or Firm* — Ropes & Gray LLP; James F. Haley, Jr.; Yang Xu

(57) ABSTRACT

An object of the present invention is to provide a novel integrase inhibitor. The present invention relates to a novel compound having an antiviral effect, more specifically, a pyridone derivative having HIV integrase inhibitory activity, and a medicament containing the same, in particular, an anti-HIV agent. The compound of the present invention has integrase inhibitory activity and/or cell proliferation inhibitory activity against viruses, in particular, HIV and drug-resistant strains thereof. Thus, the compound is useful in preventing or treating various diseases, viral infections (for example, AIDS), and the like in which integrase participates.

16 Claims, No Drawings

PYRIDONE DERIVATIVE HAVING INTEGRASE INHIBITORY ACTIVITY

This application is a national stage application under 35 U.S.C. §371 of International Application PCT/JP2011/002139, filed Apr. 11, 2011, which application claims priority from Japanese Application 2010-91387, filed Apr. 12, 2010. The disclosure of each of these referenced applications is incorporated by reference herein in its entirety.

TECHNICAL FIELD

The present invention relates to novel compounds having antiviral activity, more particularly, pyridone derivatives having HIV integrase inhibitory activity; and a medicament containing the same, particularly an anti-HIV agent.

BACKGROUND ART

Among viruses, human immunodeficiency virus (hereafter, referred to as HIV), a kind of retrovirus, is known to cause acquired immunodeficiency syndrome (hereafter, referred to as AIDS). The therapeutic agent for AIDS is mainly selected from a group of reverse transcriptase inhibitors (e.g., AZT, 3TC, etc.) and protease inhibitors (e.g., Indinavir, etc.), but they are proved to be accompanied by the following problems: side effects such as nephropathy, the emergence of resistant viruses, and the like. Thus, the development of anti-HIV agents having the other mechanisms of action therefrom has been desired.

On the other hand, currently, a multiple combination therapy is reported to be efficient in treatment for AIDS because of the frequent emergence of the resistant mutant virus. Two kinds of reverse transcriptase inhibitors and protease inhibitors are clinically used as an anti-HIV agent; however agents having the same mechanism of action often exhibit cross-resistance or only an additional activity. Therefore, development of anti-HIV agents having the other mechanism of action is desired.

Under the circumstances above, an integrase inhibitor has been focused on as an anti-HIV agent having a novel mechanism of action (Ref: Patent Documents 1 and 2). As an anti-HIV agent having such a mechanism of action, known are carbamoyl-substituted hydroxypyrimidinone derivative (Ref: Patent Document 3) and carbamoyl-substituted hydroxypyrrolidione derivative (Ref: Patent Document 4). Further, a patent application concerning carbamoyl-substituted hydroxypyridone derivative has been filed (Ref: Patent Document 5, Example 8).

Further, other known carbamoylpyridone derivatives include 5-alkoxypyridine-3-carboxamide derivatives and γ-pyrone-3-carboxamide derivatives, which are a plant growth inhibitor or herbicide (Ref: Patent Documents 6-8).

Furthermore, other HIV integrase inhibitors include nitrogen-containing condensed cyclic compounds (Ref: Patent Document 9).

Moreover, other HIV integrase inhibitors are known, and in such compounds, the terminal of an amide side chain is aryl (Ref: Patent Documents 10 and 11).

In addition, the present applicant filed a patent application of an anti-influenza agent comprising a nitrogen-containing condensed cyclic compound as an active ingredient (Japanese Patent Application No.: 2009-142166).

PRIOR ART REFERENCES

Patent Document

[Patent Document 1] International Publication No. 03/016275
[Patent Document 2] International Publication No. 2004/024693
[Patent Document 3] International Publication No. 03/035076
[Patent Document 4] International Publication No. 2004/004657
[Patent Document 5] Japanese Laid-Open Publication No. 2004-244320
[Patent Document 6] Japanese Laid-Open Publication No. 2-108668
[Patent Document 7] Japanese Laid-Open Publication No. 2-108683
[Patent Document 8] Japanese Laid-Open Publication No. 2-96506
[Patent Document 9] International Publication No. 2005/016927
[Patent Document 10] International Publication No. 2006/116764
[Patent Document 11] International Publication No. 2007/049675

SUMMARY OF THE INVENTION

Problems to be Solved by the Invention

Under such the circumstances, the development of a novel integrase inhibitor has been desired.

Means to Solve the Problems

The present inventors intensively studied to find that a novel pyridone derivative has potent HIV integrase inhibitory activity. Moreover, the present inventors have discovered that a compound of the present compound and a medicament containing the same are useful as an antiviral agent (e.g., antiretroviral agent, anti-HIV agent, anti-HTLV-1 (Human T cell leukemia virus type 1) agent, anti-FIV (Feline immunodeficiency virus) agent, anti-SIV (Simian immunodeficiency virus) agent), especially an anti-HIV agent, an anti-AIDS agent, a therapeutic for associated diseases, or the like, to accomplish the present invention shown below.

(1) A compound of the formula:

[Chemical formula 1]

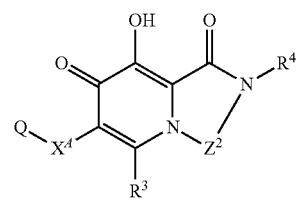

(QI)

(wherein
R$^4$ is hydrogen, optionally substituted lower alkyl (with the proviso that the substituent is not optionally substituted aryl), optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substitutedaryloxy, optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, $NR^a$ (wherein $R^a$ is hydrogen or lower alkyl), —N═, and ═N—);

$Z^2$ is optionally substituted lower alkylene or optionally substituted lower alkenylene that may be intervened by a heteroatom group selected from the group consisting of O, S, SO, $SO_2$, $NR^5$ (wherein $R^5$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, $NR^5$ (wherein $R^5$ is, independent of $R^4$, selected from the same substituent group as $R^4$), —N═, and ═N—)), —N═, and ═N—;

$X^A$ is a group selected from the following group:
$X^{A1}$: a single bond;
$X^{A2}$: a group selected from C═O and C═S;
$X^{A3}$: a heteroatom group selected from O, S, SO, $SO_2$, and $NR^{1'}$ wherein $R^{1'}$ is hydrogen or lower alkyl;
$X^{A4}$: a group formed by linking the same or different, two or more groups selected from $X^{A2}$ and $X^{A3}$;
$X^{A5}$: a group selected from —N═N—, —C($R^{1'}$)═N—, or —N═C($R^{1'}$)— wherein $R^{1'}$ is hydrogen or lower alkyl;
$X^{A6}$: optionally substituted lower alkylene or optionally substituted lower alkenylene;
$X^{A7}$: $X^{A6}$ intervened by one or any two or more groups selected from $X^{A2}$, $X^{A3}$, $X^{A4}$, and $X^{A5}$; and
$X^{A8}$: a spacer consisting of any combination of $X^{A1}$ to $X^{A7}$;

Q is a group selected from the following group:
$Q^1$: a carbocyclic group that may be substituted and may be condensed; and
$Q^2$: a heterocyclic group that may be substituted and may be condensed,
with the proviso that the case where —$X^A$-Q is —$CONR^1$—X—$R^2$ (wherein
$R^1$ is hydrogen or lower alkyl;
X is a single bond; a heteroatom group selected from O, S, SO, $SO_2$, and NH; or lower alkylene or lower alkenylene that may be intervened by the heteroatom group; and
$R^2$ is optionally substituted aryl) is excluded;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino;

$R^4$ may be taken together with the $Z^2$ part to form a ring, and in this case, Compound (QI) is represented by the following formula (QI-1) or (QI-11):

[Chemical formula 2]

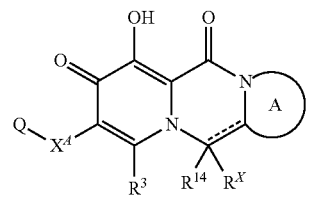

(QI-1)

(wherein
the A ring is an optionally substituted heterocycle; $R^{14}$ and $R^X$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (wherein the lower alkyl may be intervened by a heteroatom group selected from the group consisting of O, S, SO, $SO_2$, $NR^5$ (wherein $R^5$ is, independent of $R^4$, selected from the same substituent group as $R^4$), —N═, and ═N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, or optionally substituted aminocarbonyl; the broken line represents the presence or absence of a bond; with the proviso that when the broken line represents the presence of a bond, $R^X$ is not present;

$X^A$ and Q are defined the same as above;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino);

[Chemical formula 3]

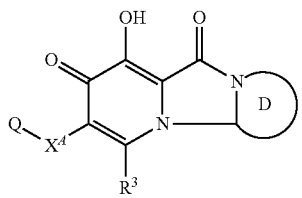

(QI-11)

(wherein
the D ring is an optionally substituted heterocycle;
$X^A$ and Q are defined the same as above;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino);
alternatively, $Z^2$ may be a linking group consisting of $B^1$ and $B^2$, and in this case, Compound (QI) is represented by the following formula (QI-B):

[Chemical formula 4]

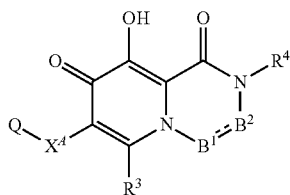

(QI-B)

(wherein
the broken line represents the presence or absence of a bond;
either one of $B^1$ and $B^2$ is $CR^{20}R^{21}$ and the other is $NR^{22}$, and in this case, the broken line is not present;
when $B^2$ is $NR^{22}$, $R^4$ and $R^{22}$ may be taken together to form an optionally substituted heterocycle;
when $B^2$ is $CHR^{21}$, $R^4$ and $R^{21}$ may be taken together to form an optionally substituted heterocycle;
or $B^1$ and $B^2$ are each independently C, $CR^{23}$, or N, and in this case, the $B^1$ and $B^2$ parts may be taken together to form an optionally substituted heterocycle;
$R^{20}$, $R^{21}$, $R^{22}$, and $R^{23}$ are each independently, hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (wherein the lower alkyl may be intervened by a heteroatom group selected from the group consisting of O, S, SO, $SO_2$, $NR^5$ (wherein $R^5$ is, independent of $R^4$, selected from the same substituent group as $R^4$), —N=, and =N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl; and
other symbols are defined the same as above)),
or a pharmaceutically acceptable salt thereof, or a solvate thereof.

(2) The compound according to (1), or a pharmaceutically acceptable salt thereof, or a solvate thereof, wherein $X^A$ in —$X^A$-Q is —$CONR^{1'}$—, —$CONR^{1'}$—$X^{46}$—, or —$CONR^{1'}$—$X^{47}$— in which each symbol is defined the same as above.

(3) The compound according to claim (1) or (2), or a pharmaceutically acceptable salt thereof, or a solvate thereof, wherein Q is $Q^2$: a heterocyclic group that may be substituted and may be condensed.

(4) The compound according to any of (1) to (3), or a pharmaceutically acceptable salt thereof, or a solvate thereof, wherein Q is a 5- to 7-membered heterocyclic group which may be substituted, may be condensed, and contains one to four heteroatoms that are one or the same or different, two or more heteroatoms selected from O, S and N atoms.

(5) The compound according to any of (1) to (4), or a pharmaceutically acceptable salt thereof, or a solvate thereof, wherein Q is $Q^1$: a carbocyclic group that may be substituted and may be condensed.

(6) The compound according to any of (1) to (5), or a pharmaceutically acceptable salt thereof, or a solvate thereof, wherein Q is cycloalkyl that may be substituted and may be condensed.

(7) The compound according to any of (1) to (6), or a pharmaceutically acceptable salt thereof, or a solvate thereof, wherein $X^A$ in —$X^A$-Q is —$CONR^{1'}$—, —$CONR^{1'}$—$X^{46}$—, or —$CONR^{1'}$—$X^{47}$— in which each symbol is defined the same as above; Q is $Q^2$: a heterocyclic group that may be substituted and may be condensed, or cycloalkyl that may be substituted and may be condensed.

(8) The compound according to any of (1) to (7), or a pharmaceutically acceptable salt thereof, or a solvate thereof, wherein $R^3$ is hydrogen.

(9) The compound according to any of (1) to (8), or a pharmaceutically acceptable salt thereof, or a solvate thereof, wherein Compound (QI) is of formula (QI-1), (QI-11), or (QI-B).

(10) The compound according to any of (1) to (9), or a pharmaceutically acceptable salt thereof, or a solvate thereof, wherein Compound (QI) is of formula (QI-1); $R^3$, $R^{14}$, and $R^X$ are hydrogen; and the broken line represents the absence of a bond.

(11) A pharmaceutical composition comprising a compound according to any of (1) to (10), or a pharmaceutically acceptable salt thereof, or a solvate thereof.

(12) The pharmaceutical composition according to (11), which is an anti-HIV agent.

(13) The pharmaceutical composition according to (11) or (12), which is an integrase inhibitor.

(14) A method for treating viral infection (in particular, HIV infection), characterized by administering to a human an antivirally effective amount of a compound according to any of (1) to (10).

(15) The compound according to any of (1) to (10) for the use in medicinal treatment.

(16) Use of the compound according to any of (1) to (10) to produce a medicament for preventing or treating viral infection (in particular, HIV infection).

(17) A method, a system, an apparatus, a kit, and the like for producing the compound according to any of (1) to (10), or a pharmaceutically acceptable salt thereof, or a solvate thereof.

(18) A method, a system, an apparatus, a kit, and the like for preparing a pharmaceutical composition comprising the compound according to any of (1) to (10), or a pharmaceutically acceptable salt thereof, or a solvate thereof.

(19) A method, a system, an apparatus, a kit, and the like using the compound the compound according to any of (1) to (10), or a pharmaceutically acceptable salt thereof, or a solvate thereof.

Effect of the Invention

The compound of the present invention has integrase inhibitory activity and/or cell proliferation inhibitory activity against viruses, in particular, HIV and drug-resistant strains thereof. Thus, the compound is useful in preventing or treating various diseases, viral infections (e.g., AIDS), and the like in which integrase participates. More preferably, it is difficult for the compound of the present invention to cause a new HIV-resistant virus. Further preferably, the compound of the present invention is useful as a medicament that is excellent in solubility, peroral absorbability, metabolic stability, bioavailability or the like, and for which there is little concern about cytotoxicity and a side effect (e.g., mutagenicity, the QT interval prolongation of the electrocardiogram).

MODE FOR CARRYING OUT THE INVENTION

The terms used herein are explained below. Each term, alone or in combination with another term, means as follows.

"Lower alkylene" means a linear or branched $C_{1-6}$ lower alkylene such as methylene, ethylene, trimethylene, propylene, tetramethylene, ethylethylene, pentamethylene, hexamethylene, or the like. Preferred is a $C_{1-4}$ linear lower alkylene such as methylene, ethylene, trimethylene, or tetramethylene. More preferred is methylene or ethylene.

"Lower alkenylene" means a linear or branched $C_{2-6}$ lower alkenylene group, which consists of the above "Lower alkylene" having one or more double bonds, such as vinylene, propylene, or butenylene. Preferred is a $C_{2-3}$ linear lower alkenylene such as vinylene or propylene.

"Alkyl" means a linear or branched $C_{1-10}$ alkyl group such as methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, n-decyl, and the like. Preferred is a $C_{1-6}$ lower alkyl and more preferred is a $C_{1-4}$ lower alkyl, such as methyl, ethyl, n-propyl, isopropyl, n-butyl, isobutyl, sec-butyl, tert-butyl, n-pentyl, isopentyl, neopentyl, tert-pentyl, n-hexyl, and isohexyl.

When lower alkyl is intervened by —N═ or ═N—, the lower alkyl may have a double bond to form, for example, —CH$_2$—N═CH$_2$, —CH═N—CH$_3$, or the like.

"Alkenyl" means a linear or branched $C_{2-8}$ alkenyl, which consists of the above "alkyl" having one or more double bonds, such as vinyl, 1-propenyl, 2-propenyl, 1-butenyl, 2-butenyl, 3-butenyl, 1,3-butadienyl, 3-methyl-2-butenyl, and the like. Preferred is $C_{2-6}$ lower alkenyl, and more preferred is $C_{2-4}$ lower alkenyl.

"Lower alkenyloxy" means an oxy attached to the above "lower alkenyl", such as vinyloxy, 1-propenyloxy, 2-propenyloxy, 1-butenyloxy, 2-butenyloxy, 3-butenyloxy, 1,3-butadienyloxy, 3-methyl-2-butenyloxy, and the like.

"Alkynyl" means a linear or branched $C_{2-8}$ alkenyl, which consists of the above "alkyl" having one or more triple bonds, such as ethynyl, propargyl, and the like. Preferred is $C_{2-6}$ lower alkynyl, and more preferred is $C_{2-4}$ lower alkynyl.

"Carbocyclic group" means a saturated or unsaturated $C_{3-10}$ carbocyclic group, and includes cycloalkyl, cycloalkenyl, and aryl.

"Cycloalkyl" means a $C_{3-10}$ cyclic saturated hydrocarbon group, such as cyclopropyl, cyclobutyl, cyclopentyl, cyclohexyl, cyclopentyl, cyclooctyl, and the like. Preferred is $C_{3-6}$ cycloalkyl.

"Cycloalkyl lower alkyl" means a lower alkyl substituted with the above cycloalkyl, such as cyclopropylmethyl, cyclopropylethyl, cyclobutylmethyl, cyclopentylmethyl, cyclohexylmethyl, cyclohexylethyl, and the like. Preferred is $C_{3-6}$ cycloalkyl lower alkyl.

"Aryl" means a monocyclic aromatic hydrocarbon group (phenyl) and a polycyclic aromatic hydrocarbon (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, and the like). Preferred is phenyl or naphthyl (e.g., 1-napthyl, 2-naphthyl).

"Aralkyl" or "aryl lower alkyl" means the above "lower alkyl" substituted with one to three of the above "aryl", such as benzyl, diphenylmethyl, triphenylmethyl, phenethyl, 1-napthylmethyl, 2-napthylmethyl, and the like. Preferred is benzyl.

"Aryloxy" means an oxy attached to the above "aryl", such as 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy, 9-phenanthryloxy, and the like. Preferred is phenyloxy or naphthyloxy (e.g., 1-napthyloxy, 2-naphthyloxy).

"Heterocyclic group" means "heteroring" or "heteroaryl".

"Heteroring" means a non-aromatic heterocyclic group (preferably 5- to 7-membered ring) which has at least one of nitrogen, oxygen, phosphorus and/or sulfur atoms in the ring and may be bonded at any substitutable position such as 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperadinyl, 2-piperadinyl, 2-morpholinyl, 3-morpholinyl, morpholino, tetrahydropyranyl, and the like. The "non-aromatic heterocyclic group" is a saturated or unsaturated ring.

"Heteroaryl" means a monocyclic aromatic heterocyclic group or a condensed aromatic heterocyclic group.

Monocyclic aromatic heterocyclic group means a group derived from a 5- to 8-membered aromatic ring optionally containing one to four of oxygen, sulfur, phosphorus and/or nitrogen atoms in the ring wherein the group may be bonded at any substitutable position.

Condensed aromatic heterocyclic group means a group wherein a 5- to 8-membered aromatic ring optionally containing one to four of oxygen, sulfur, phosphorus and/or nitrogen atoms in the ring is condensed with one to four of 5- to 8-membered aromatic carbocycle(s) or the other 5- to 8-membered aromatic heterocycle(s), and wherein the group may be bonded at any substitutable position.

Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzoimidazolyl, 2-benzoimidazolyl, 4-benzoimidazolyl, 5-benzoimidazolyl), dibenzofuryl, benzoxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), purinyl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl), phenothiazinyl (e.g., 1-phenothiazinyl, 2-phenothiazinyl, 3-phenothiazinyl, 4-phenothiazinyl), or the like.

"Heterocycle" and "heterocyclic ring" mean a ring from which the above heterocyclic group can be derived.

"Heterocyclic lower alkyl" and "heterocyclyl lower alkyl" mean lower alkyl substituted with the above "heterocyclic group".

"Heterocyclyloxy" means an oxy attached to the above "heterocyclic group".

"Lower alkoxy" or "alkoxy" mean an oxy attached to the above "lower alkyl" or "alkoxy", such as methoxy, ethoxy, n-propoxy, isopropoxy, n-butoxy, isobutoxy, tert-butoxy, and the like.

"Lower alkylcarbonyl", "cycloalkylcarbonyl", "cycloalkyl lower alkylcarbonyl", "lower alkoxycarbonyl", "arylcarbonyl", "aryl lower alkylcarbonyl", "aryloxycarbonyl", "heterocyclylcarbonyl", "heterocyclyl lower alkylcarbonyl", and "heterocyclyloxycarbonyl" means a carbonyl attached to the above "lower alkyl", "cycloalkyl", "cycloalkyl lower alkyl", "lower alkoxy", "aryl", "aryl lower alkyl", "aryloxy", "heterocyclic group", and "heterocyclyl lower alkyl", respectively.

When a substituent(s) is/are present on "optionally substituted lower alkyl", "optionally substituted cycloalkyl", "optionally substituted cycloalkyl lower alkyl", "optionally substituted lower alkenyl", "optionally substituted lower alkynyl", "optionally substituted lower alkoxy", "optionally substituted aryl", "optionally substituted aryl lower alkyl", "optionally substituted aryloxy", "optionally substituted heterocycle", "optionally substituted heterocyclic group", "optionally substituted heterocyclyl lower alkyl", "optionally substituted heterocyclyloxy", "optionally substituted lower alkenyloxy", "optionally substituted lower alkylcarbonyl", "optionally substituted cycloalkylcarbonyl", "optionally substituted cycloalkyl lower alkylcarbonyl", "optionally substituted lower alkoxycarbonyl", "optionally substituted arylcarbonyl", "optionally substituted aryl lower alkylcarbonyl", "optionally substituted aryloxycarbonyl", "optionally substitutedheterocyclylcarbonyl", "optionally substituted heterocyclyl lower alkylcarbonyl", "optionally substituted heterocyclyloxycarbonyl", "optionally substituted lower alkylene", "optionally substituted lower alkenylene", "optionally substituted phosphoric acid residue", "optionally substituted carbocycle" or the like, each may be substituted with the same or different, 1 to 4 group(s) selected from Substituent group B (described below) at any position.

Examples of Substituent group B include hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy), lower alkenyloxy (e.g., vinyloxy, allyloxy), lower alkoxycarbonyl (e.g., methoxycarbonyl, ethoxycarbonyl, tert-butoxycarbonyl), nitro, nitroso, optionally substituted amino (e.g., alkylamino (e.g., methylamino, ethylamino, dimethylamino), acylamino (e.g., acetylamino, benzoylamino), aralkylamino (e.g., benzylamino, tritylamino), hydroxyamino)), azido, aryl (e.g., phenyl), aralkyl (e.g., benzyl), cyano, isocyano, isocyanato, thiocyanato, isothiocyanato, mercapto, alkylthio (e.g., methylthio), alkylsulfonyl (e.g., methanesulfonyl, ethanesulfonyl), optionally substituted alkylsulfonylamino (e.g., methanesulfonylamino, ethanesulfonylamino, N-methylsulfonyl-N'-methylamino), optionally substituted carbamoyl (e.g., alkylcarbamoyl (e.g., methylcarbamoyl, ethylcarbamoyl, dimethylcarbamoyl)), sulfamoyl, acyl (e.g., formyl, acetyl), formyloxy, haloformyl, oxalo, thioformyl, thiocarboxy, dithiocarboxy, thiocarbamoyl, sulfino, sulfo, sulfoamino, hydrazino, azido, ureido, amidino, guanidino, phthalimido, oxo, phosphoric acid residue, phosphoric-acid-residue-substituted lower alkyl (which may be intervened by a heteroatom group(s)), aryl substituted with a phosphoric acid residue, aralkyl substituted with a phosphoric acid residue, hydroxy lower alkyl and the like, more preferably hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkoxy (e.g., methoxy, ethoxy, propoxy, butoxy), optionally substituted amino (e.g., alkylamino (e.g., methylamino, ethylamino, dimethylamino)), oxo, phosphoric acid residue, and the like.

Examples of a substituent (s) of "optionally substituted amino" or "optionally substituted carbamoyl" include mono- or di-lower alkyl, lower alkylcarbonyl, or lower alkylsulfonyl, optionally substituted lower alkyl (e.g., methyl, ethyl, isopropyl, benzyl, carbamoylalkyl (e.g., carbamoylmethyl), mono- or di-lower alkylcarbamoyl lower alkyl (e.g., dimethylcarbamoylethyl), hydroxy lower alkyl, heterocyclyl lower alkyl (e.g., morpholinoethyl, tetrahydropyranylethyl), alkoxycarbonyl lower alkyl (e.g., ethoxycarbonylmethyl, ethoxycarbonylethyl), mono- or di-lower alkylamino lower alkyl (e.g., dimethylaminoethyl)), lower alkoxy lower alkyl (e.g., methoxyethyl, ethoxymethyl, ethoxyethyl, isopropoxy-ethyl, and the like), acyl (e.g., formyl, optionally substituted lower alkylcarbonyl (e.g., acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl), lower alkoxy lower alkylcarbonyl (e.g., methoxyethylcarbonyl), lower alkylcarbamoyl lower alkylcarbonyl (e.g., methylcarbamoylethylcarbonyl), alkoxycarbonylacetyl), optionally substituted arylcarbonyl (e.g., benzoyl, toluoyl), optionally substituted aralkyl (e.g., benzyl, 4-fluorobenzyl), hydroxy, optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), arylsulfonyl optionally substituted with lower alkyl or halogen (e.g., benzenesulfonyl, toluenesulfonyl, 4-fluorobenzenesulfonyl), cycloalkyl (e.g., cyclopropyl), aryl optionally substituted with lower alkyl (e.g., phenyl, trityl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methyl sulfamoyl, dimethylsulfamoyl), lower alkylcarbonylamino (e.g., methylcarbonylamino), heterocycle (e.g., morpholino, tetrahydropyranyl), optionally substituted amino (e.g., mono- or di-alkylamino (e.g., dimethylamino), formylamino), and the like.

As to an amino group of "optionally substituted amino", "optionally substituted aminocarbonyl", or "optionally substituted carbamoyl", two substituents on the amino group together with the adjacent nitrogen atom may form a nitrogen-containing heterocycle which may contains sulfur and/or oxygen atoms in the ring (preferably 5- to 7-membered ring, also preferably saturated ring) and the ring is optionally substituted with oxo or hydroxy. The sulfur atom forming the ring may be substituted with oxo. A 5- or 6-membered ring and the like such as piperazinyl, piperidino, morpholino, pyrrolidino, 2-oxopiperidino, 2-oxopyrrolidino, 4-hydroxymorpholino and the like are preferred.

"Phosphoric acid residue" means a group represented by the formula: —PO(OH)$_2$. "Optionally substituted phosphoric acid residue" means a phosphoric acid residue in which the OH part and/or hydrogen of the OH may be substituted, and the phosphoric acid residue is preferably represented by the following formula:

[Chemical formula 5]

(P-1)

wherein, $R^A$ and $R^B$ are each independently $OR^C$ or $NR^D R^E$ (wherein $R^C$, $R^D$ and $R^E$ are each independently hydrogen, optionally substituted lower alkyl, optionally substituted cycloalkyl, optionally substituted aryl, optionally substituted heterocyclic group, or $R^D$ and $R^E$ taken together with the adjacent N atom may form an optionally substituted heterocycle (preferably 5- to 6-membered ring)), or $R^A$ and $R^B$ taken together with the adjacent P atom may form an optionally substituted heterocycle (preferably 5- to 6-membered ring).

More preferably, $R^A$ and $R^B$ are both $OR^C$, or either one of them is $OR^C$ and the other is $NR^D R^E$.

$R^C$, $R^D$, and $R^E$ are, preferably, each independently lower alkyl (e.g., methyl, ethyl).

The optionally substituted heterocycle formed by $R^A$ and $R^B$ taken together with the adjacent P atom may be the following structure:

[Chemical formula 6]

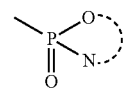

wherein the broken line means a part of the ring.

"Hydroxy substituted with optionally substituted phosphoric acid residue" is preferably hydroxy substituted with a phosphoric acid residue substituted with di-lower alkyls, and more preferably a group of the following formula:

[Chemical formula 7]

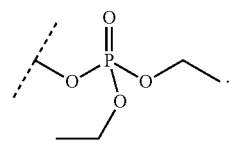

"Amino substituted with optionally substituted phosphoric acid residue" is preferably amino substituted with a phosphoric acid residue substituted with di-lower alkyls, and more preferably a group of the following formula:

[Chemical formula 8]

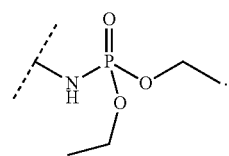

"Aryl substituted with optionally substituted phosphoric acid residue", "aralkyl substituted with optionally substituted phosphoric acid residue", and "lower alkyl substituted with optionally substituted phosphoric acid residue" mean aryl, aralkyl, and lower alkyl substituted with the above "optionally substituted phosphoric acid residue", respectively. The above lower alkyl may be intervened by a heteroatom group selected from the group consisting of O, S, SO, SO$_2$, NR$^5$ (wherein R$^5$ is, independent of R$^4$, selected from the same substituent group as R$^4$), —N=, and =N—.

"Aryl substituted with optionally substituted phosphoric acid residue" is preferably phenyl substituted with phosphoric acid residue substituted with di-lower alkyls.

"Aralkyl substituted with optionally substituted phosphoric acid residue" herein is preferably benzyl substituted with phosphoric acid residue substituted with di-lower alkyls.

"Lower alkyl substituted with optionally substituted phosphoric acid residue" herein is preferably methyl substituted with phosphoric acid residue substituted with di-lower alkyls.

MORE PREFERRED EMBODIMENTS

In —$X^A$-Q, $X^A$ is a group selected from the following group:
$X^{A1}$: a single bond;
$X^{A2}$: C=O;
$X^{A3}$: a heteroatom selected from O, S, SO, $SO_2$, and $NR^{1'}$ wherein
$R^{1'}$ is hydrogen or lower alkyl;
$X^{A4}$: a group formed by linking the same or different, two or more groups selected from $X^{A2}$ and $X^{A3}$ (e.g., —CONH—, —CONHNH—, —CONHNHCO—, —CONHO—, —CONHNHSONH—, —CONHNMe-, —NHCONH—, —NHCOO—);
$X^{A5}$: a group selected from —N=N—, —C($R^{1'}$)=N—, or —N=C($R^{1'}$)— wherein $R^{1'}$ is hydrogen or lower alkyl;
$X^{A6}$: optionally substituted lower alkylene or optionally substituted lower alkenylene (example of substituent: Me, Ph);
$X^{A7}$: $X^{A6}$ intervened by one or any two or more groups selected from $X^{A2}$, $X^{A3}$, $X^{A4}$, and $X^{A5}$ (e.g., —$CONHCH_2$—, —$CONMeCH_2$—, —$CONHCH_2CH_2O$—, —$CONHCH_2CH_2$—$SO_2$-, —$CONHCH_2CH_2CH_2$—); and
$X^{A8}$: a spacer consisting of any combination of $X^{A1}$ to $X^{A7}$.

In $X^A$, "intervene" may be any of cases where one or any two or more groups selected from $X^{A2}$, $X^{A3}$, $X^{A4}$, and $X^{A5}$ 1) are present between carbon atoms carbon atoms constituting lower alkylene or lower alkenylene, 2) are present at an end of lower alkylene or lower alkenylene, and where 1) and 2) coexist.

$X^A$ is a spacer consisting of, preferably, one to five atoms linked, and more preferably, one to three atoms linked.

$X^A$ is preferably —$CONR^{1'}$—, —$CONR^{1'}$—$X^{A6}$—, or —$CONR^{1'}$—$X^{A7}$— wherein each symbol is defined the same as above.

$X^A$ is more preferably —$CONHCH_2$—.

$R^{1'}$ is hydrogen or lower alkyl, and preferably hydrogen.

Q is a group selected from the following group:
$Q^1$: a carbocyclic group that may be substituted and may be condensed; and
$Q^2$: a heterocyclic group that may be substituted and may be condensed.

Q is preferably $Q^2$: a heterocyclic group that may be substituted and may be condensed.

Q is more preferably a 5- to 7-membered heterocyclic group that may be substituted, may be condensed, and contains one to four heteroatoms that are one or the same or different, two or more heteroatoms selected from O, S, and N atoms.

Q is preferably $Q^1$: a carbocyclic group that may be substituted and may be condensed.

Q is more preferably cycloalkyl that may be substituted and may be condensed.

The carbocyclic group of $Q^1$ is preferably cycloalkyl (preferably 5- to 7-membered). Examples of a condensed ring thereof include a benzene ring and monocyclic heterocycle (preferably 5- to 7-membered).

The heterocyclic group of $Q^2$ is preferably a monocyclic heterocyclic group (preferably 5- to 7-membered), more preferably a monocyclic aromatic heterocyclic group (e.g., thienyl, furyl, thiazolyl, imidazolyl, pyridyl, oxazolyl, isoxazolyl, pyrazinyl, and preferably thiophene, furan). Further, the monocyclic heterocyclic group may be a non-aromatic heterocyclic group (e.g., morpholinyl, thiomorpholinyl, pyrrolidyl, piperidyl, piperazyl, oxazolinyl). Examples of a condensed ring of these monocyclic heterocyclic groups include a benzene ring and other monocyclic heterocycles (preferably 5- to 7-membered).

Examples of a substituent(s) of "may be substituted" in Q include the same or different, one to three, preferably one or two, substituents selected from the group consisting of, preferably, halogen, hydroxy, amino, lower alkylamino, cyano, carboxy, formyl, oxo, lower alkyl, lower alkoxy, lower alkylthio, carbamoyl, lower alkylcarbamoyl, phenyloxy, aryl, aralkyl, aryloxy, lower alkylenedioxy, lower alkenyl, lower alkynyl, methylsulfonyl, and Substituent group S1 described below. More preferred are halogen, hydroxy, amino, cyano, lower alkyl, and lower alkoxy. In addition, such a substituent may be a spiro ring (preferably 5- to 7-membered) that may be condensed to a benzene ring or the like.

Substituent group S1: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (wherein the lower alkyl may be intervened by a heteroatom group selected from the group consisting of CO, O, S, SO, $SO_2$, $NR^a$ (wherein $R^a$ is hydrogen or lower alkyl), —N=, and =N—), lower alkoxy lower alkyl, optionally substituted amino lower alkyl (substituent: mono- or di-lower alkyl, lower alkylcarbonyl, or lower alkylsulfonyl), halogenated lower alkyl, lower alkoxy, optionally substituted carbamoyl (substituent: mono- or di-lower alkyl, lower alkylcarbonyl, or lower alkylsulfonyl), optionally substituted lower alkylsulfonylamino, halogenated lower alkoxy, and hydroxy lower alkyl.

$Q^2$ is more preferably a heterocyclic group (preferably 5- to 7-membered) that may be substituted and may be condensed, or cycloalkyl (preferably 5- to 7-membered) that may be substituted and may be condensed.

$R^3$ may be a variety of substituents as far as they do not adversely affect on the pharmacological activity of Compound (QI). Examples thereof include, for example, hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, and optionally substituted amino. Examples of a substituent(s) of "optionally substituted" include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclic group, lower alkylcarbonyl, lower alkylcarbonyloxy, lower alkoxycarbonyl, halogenated lower alkyl, halogenated lower alkoxy, and the like. More preferred are halogen, hydroxy, amino, lower alkylamino, lower alkyl, lower alkoxy, and the like. $R^3$ is more preferably hydrogen, halogen, hydroxy, lower alkyl, lower alkenyl, lower alkoxy, lower alkenyloxy, or optionally substituted amino, further preferably hydrogen or lower alkyl (e.g., methyl), and particularly preferably hydrogen.

$Z^2$ represents preferably C, CH, optionally substituted lower alkylene, lower alkenylene, or the like, and $Z^2$ and $R^4$ may be taken together to form a ring. In this case, Compound (QI) represents a tricyclic compound shown with the following Compound (QI-1) or (QI-11), or a tetracyclic compound, which is a derivative therefrom.

[Chemical formula 9]

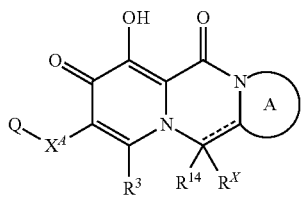
(QI-1)

[Chemical formula 10]

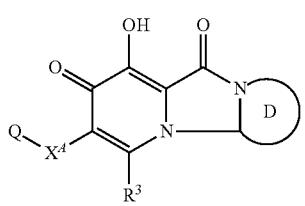
(QI-11)

The A ring is an optionally substituted heterocycle containing at least one N atom. The heterocycle is preferably a 5- to 7-membered ring containing one to three, preferably two or three, O, S and/or N atoms, and more preferably is selected from the foregoing heterocycles. One of preferred embodiments of the A ring is an optionally substituted ring described below:

[Chemical formula 11]

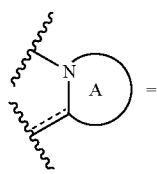 =

(a)
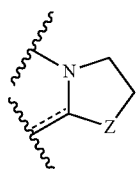

(b)
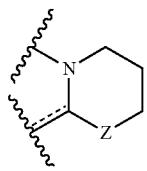

(c)
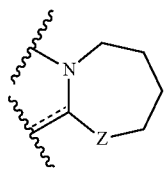

(d)
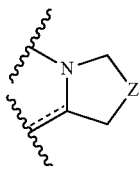

(e)
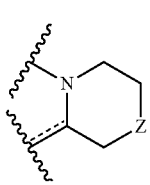

(f)
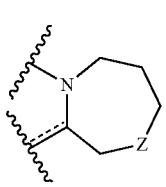

(g)
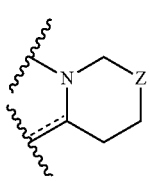

(h)
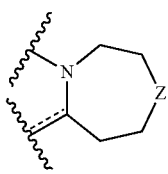

(i)
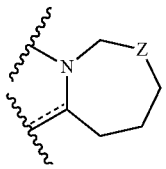

wherein Z is $CH_2$, O, S, SO, $SO_2$, or $NR^{19}$.

The A ring is preferably a ring of (a), (b) or (c).

One of preferred embodiments of Z is O or $NR^{19}$.

When $Z=NR^{19}$, $R^{19}$ is preferably, 1) hydrogen, 2) optionally substituted lower alkyl (example of substituent: amino optionally substituted with mono- or di-lower alkyl, cycloalkyl, hydroxy, optionally substituted heterocyclic group (wherein the heterocycle is preferably a 5- to 7-membered ring; example: furyl, thienyl, thiazolyl, pyridyl, morpholino, imidazole; example of substituent: lower alkyl, halogen), optionally substituted heterocyclylcarbonyl (wherein the heterocycle is preferably a 5- to 7-membered ring; example: morpholinocarbonyl), optionally substituted phenyl (substituent: lower alkyl, amino, lower alkylamino, hydroxy, halogen, halogenated lower alkyl, lower alkoxy, halogenated lower alkoxy, lower alkylthio, lower alkylsulfonyl), acetylamino, carbamoyl, mono- or di-lower alkyl-substituted carbamoyl, lower alkylsulfonylamino, lower alkoxy, carbonyl, halogen, thiol, lower alkylthio), 3) lower alkenyl, 4) acyl (e.g., lower alkylcarbonyl), or 5) lower alkylsulfonyl. $R^{19}$ may be selected from the Substituent group S2 described below.

Another substituent on the A ring may be selected from $R^{15}$ to $R^{18}$ or the Substituent group S2 described below, and is preferably lower alkyl. Alternatively, a substituent part on the A ring may form a ring such as condensed ring, spiro ring, or the like, as described below. In this case, Compound (QI) encompasses a tetracyclic compound.

The A ring is more preferably any of the following rings:

[Chemical formula 12]

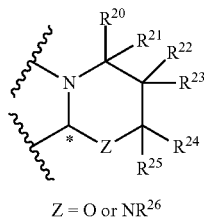
(A-1)

$Z = O$ or $NR^{26}$

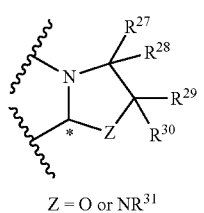
(A-2)

$Z = O$ or $NR^{31}$

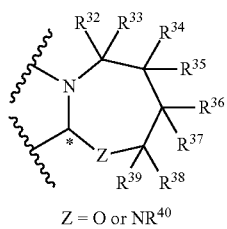
(A-3)

$Z = O$ or $NR^{40}$ wherein, each of $R^{20}$ to $R^{40}$ is independently a group selected from the Substituent group S2 described below, or any two groups of $R^{20}$ to $R^{40}$ that are attached to the same atom may be taken together with the atom to form a spiro ring (e.g., optionally substituted carbocycle or optionally substituted heterocycle), or each combination of ($R^{20}$ and $R^{22}$), ($R^{23}$ and $R^{24}$), ($R^{25}$ and $R^{26}$), ($R^{27}$ and $R^{29}$), ($R^{30}$ and $R^{31}$), ($R^{32}$ and $R^{34}$), ($R^{35}$ and $R^{36}$), ($R^{37}$ and $R^{38}$), and ($R^{39}$ and $R^{40}$) may be taken together with the adjacent atom to form an optionally substituted carbocycle or optionally substituted heterocycle.

Substituent group S2: hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, $NR^5$ (wherein $R^5$ is, independent of $R^4$, selected from the same substituent group as $R^4$), —N═, and ═N—).

The stereochemistry of an asymmetric carbon indicated by * is R- or S-configuration, or a mixture thereof.

In one embodiment, $R^{20}$ to $R^{40}$ are each independently, preferably, hydrogen, optionally substituted lower alkyl (example of substituent: OH, lower alkoxy, cycloalkyl, lower alkylthio, lower alkylsulfonyl, heterocyclic group, aryl, optionally substituted amino (example of substituent: lower alkyl, acyl)), cycloalkyl, optionally substituted aryl (example of substituent: OH, lower alkyl), or optionally substituted heterocyclic group.

In one embodiment, $R^{20}$ to $R^{25}$, $R^{27}$ to $R^{30}$, and $R^{32}$ to $R^{39}$ are each, preferably, hydrogen, $C_1$-$C_8$ alkyl, $C_6$-$C_{14}$ aryl $C_1$-$C_8$ alkyl, $C_6$-$C_{14}$ aryl or alkoxy.

In one embodiment, $R^{26}$, $R^{31}$ and $R^{40}$ are each independently, preferably, hydrogen; $C_{3-6}$ cycloalkyl; heterocycle; or $C_{1-8}$ alkyl optionally substituted with hydroxy, $C_{3-6}$ cycloalkyl, alkoxy, heteroaryl, $C_{6-14}$ aryl, or amino wherein the amino may be substituted with —$C(O)C_{1-8}$ alkyl or $C_{1-8}$ alkyl.

More preferred embodiments are illustrated below.

I) When the A ring is (A-1), preferably, 1) Z is $NR^{26}$, $R^{26}$ and $R^{24}$ are taken together to form a heterocycle, and the others are hydrogen; 2) Z is O or $NR^{26}$, ($R^{20}$ and $R^{22}$) or ($R^{23}$ and $R^{24}$) are taken together to form cycloalkyl substituted with phenyl, and the others are hydrogen or optionally substituted lower alkyl.

II) When the A ring is (A-2), preferably, 1) Z is O, $R^{27}$ or $R^{28}$ is lower alkyl, the others are hydrogen; 2) Z is $NR^{31}$, $R^{30}$ and $R^{31}$ are taken together to form a heterocycle, the others are hydrogen, or $R^{27}$ and $R^{29}$ are taken together to form cycloalkyl, and the others are hydrogen; 3) Z is O, $R^{27}$ and $R^{29}$ are taken together to form cycloalkyl optionally condensed to phenyl, and the others are hydrogen.

$R^{14}$ and $R^x$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, optionally substituted phosphoric acid residue, aryl optionally substituted with optionally substituted phosphoric acid residue, aralkyl optionally substituted with optionally substituted phosphoric acid residue, hydroxy optionally substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, SO$_2$, NR$^a$ (wherein R$^a$ is hydrogen or lower alkyl), —N=, and =N—).

R$^{14}$ and R$^x$ are each independently, preferably, hydrogen, hydroxy, optionally substituted lower alkyl (wherein the substituent is preferably, for example, amino, lower alkyl, lower alkylamino, hydroxy, or lower alkoxy). R$^{14}$ and R$^x$ are preferably hydrogen.

The broken line in Compound (QI-1) represents the presence or absence of a bond; with the proviso that when the broken line represents the presence of a bond, R$^X$ is not present.

Compound (QI-1) encompasses the following compounds:

[Chemical formula 13]

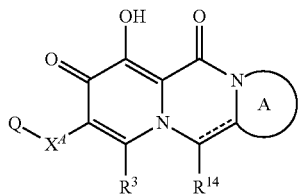

(QI-1-1)

wherein each symbol is as defined above;

[Chemical formula 14]

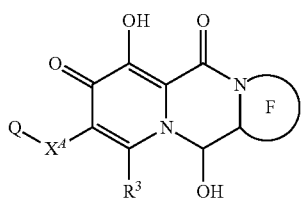

(QI-8)

wherein the F ring is the same heterocycle as the A ring, preferably a 5- to 7-membered ring, and a substituent(s) on the F ring is the same as the substituent(s) on the A ring; the other symbols are as defined above; and

[Chemical formula 15]

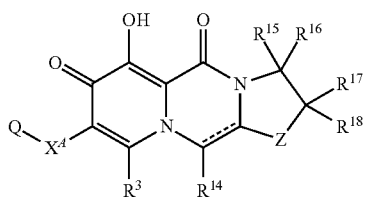

(QI-3)

wherein each symbol is as defined above; Z is O or NR$^{19}$; each of R$^{15}$ to R$^{19}$ is independently hydrogen or a group selected from the foregoing Substituent group S2, or each combination of (R$^{15}$ and R$^{16}$), (R$^{17}$ and R$^{18}$), (R$^{16}$ and R$^{18}$), and (R$^{18}$ and R$^{19}$) may be respectively taken together with the adjacent atom to form an optionally substituted carbocycle (preferably 5- to 6-membered ring) or optionally substituted heterocycle (preferably 5- to 6-membered ring); or each combination of (R$^{15}$ and R$^{16}$) and (R$^{17}$ and R$^{18}$) may be taken together to form an oxo.

Compound (QI-3) is preferably in accordance with the following embodiment:
(1) R$^{15}$ and R$^{16}$ are both hydrogen; R$^{17}$ and R$^{18}$ are both hydrogen or are taken together with the adjacent atom to form a 3- to 7-membered carbocycle; and/or Z is O or NH.

Compound (QI) further encompasses Compound (QI-11):

[Chemical formula 16]

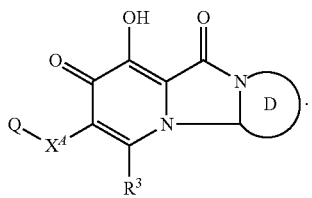

(QI-11)

The D ring means the same heterocycle as the A ring, and a 5- to 7-membered ring is preferred. A substituent(s) on the D ring is the same as that on the A ring. The other symbols are as defined above.

Compound (QI) further encompasses Compound (QI-B):

[Chemical formula 17]

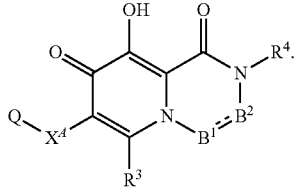

(QI-B)

R$^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino. More preferred is hydrogen or optionally substituted lower alkyl.

R$^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of O, S, SO, SO$_2$, NR$^a$ (wherein R$^a$ is hydrogen or lower alkyl), —N=, and =N—). More preferred is hydrogen, optionally substituted lower alkyl, optionally substituted cycloalkyl, optionally substituted cycloalkyl lower alkyl, optionally substituted lower alkenyl, optionally substituted aryl, optionally substituted aryl lower alkyl, optionally substituted heterocyclic group, or optionally substituted heterocyclyl lower alkyl.

The broken line represents the presence or absence of a bond.

Either one of $B^1$ and $B^2$ is $CR^{20}R^{21}$, and the other is $NR^{22}$. In this case, the broken line is not present.

When $B^2$ is $NR^{22}$, $R^4$ and $R^{22}$ may be taken together to form an optionally substituted heterocycle (e.g., G ring).

When $B^2$ is $CHR^{21}$, $R^4$ and $R^{21}$ may be taken together to form an optionally substituted heterocycle (e.g., H ring).

Alternatively, $B^1$ and $B^2$ are each independently C, $CR^{23}$, or N. $B^1$ and $B^2$ parts may be taken together to form an optionally substituted heterocycle (e.g., C ring). In this case, when $B^1$ and $B^2$ are each independently $CR^{23}$ or N, the broken line represents the absence of a bond.

$R^{20}$, $R^{21}$, $R^{22}$ and $R^{23}$ are each independently selected from hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (wherein the lower alkyl may be intervened by a heteroatom group selected from the group consisting of O, S, SO, $SO_2$, $NR^5$ (wherein $R^5$ is, independent of $R^4$, selected from the same substituent group as $R^4$), —N═, and ═N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl.

$R^{20}$, $R^{21}$, $R^{22}$, and $R^{23}$ are more preferably selected from hydrogen, optionally substituted lower alkyl, optionally substituted cycloalkyl, optionally substituted cycloalkyl lower alkyl, optionally substituted aryl, optionally substituted aryl lower alkyl, optionally substituted heterocyclic group, optionally substituted heterocyclyl lower alkyl, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl.

The above Compound (QI-B) encompassed Compound (QI-B-10), (QI-B-6), (QI-B-9) and (QI-B-12) described below.

[Chemical formula 18]

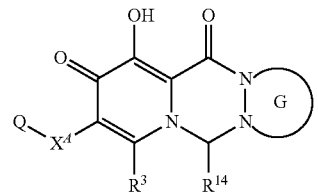

(QI-B-10)

The G ring is a 5- to 7-membered ring containing two or three O, S and/or N atoms, and contains at least two N atoms. More preferably, it is selected from the foregoing heterocycle, and the following rings are illustrated:

[Chemical formula 19]

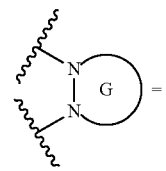

(a)

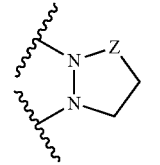

(b)

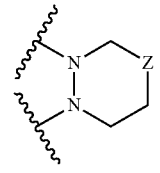

(c)

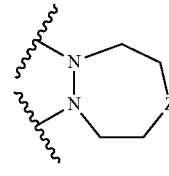

(d)

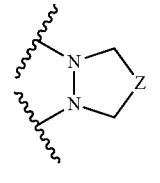

(e)

-continued

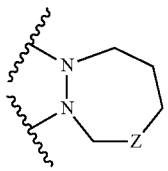

(f)

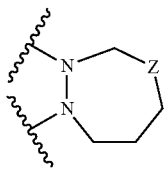

(g)

wherein Z is $CH_2$, O, S, SO, $SO_2$, or $NR^{19}$.

Examples of a substituent(s) on the G ring include the same or different, one or more substituents selected from the foregoing Substituent group S2. Alternatively, the substituent part on the G ring may be taken together with the adjacent atom to further form a condensed ring or spiro ring, preferably optionally substituted carbocycle (preferably 5- to 6-membered ring) or optionally substituted heterocycle (preferably 5- to 6-membered ring).

One of preferred embodiments of a substituent (s) on the G ring is lower alkyl (e.g., methyl, isopropyl), lower alkoxy lower alkyl (e.g., 2-methoxyethyl), optionally substituted amino (example of substituent: lower alkyl (e.g., methyl), or lower alkylcarbonyl (e.g., acetyl)).

$R^3$ is preferably hydrogen or optionally substituted lower alkyl; and more preferably hydrogen.

Examples of $R^{14}$ include the same groups as in the cases of $R^{20}$, $R^{21}$, $R^{22}$, and $R^{23}$ described above. However, $R^{14}$ is preferably hydrogen, optionally substituted lower alkyl (substituent: amino, lower alkylamino, lower alkoxy, aryloxy, cyano, halogen, (substituted) carbamoyl, acylamino, lower alkynyl, hydroxy), cycloalkyl, cycloalkyl lower alkyl, phenyl, benzyl, 5- to 6-membered aromatic heterocyclic group, 5- to 6-membered heterocyclyl lower alkyl, optionally substituted lower alkylcarbonyl (substituent: lower alkoxy), optionally substituted benzoyl (substituent: lower alkoxy), substituted sulfonyl(substituent: lower alkyl, aryl, heterocyclic group); and more preferably hydrogen or optionally substituted lower alkyl.

[Chemical formula 20]

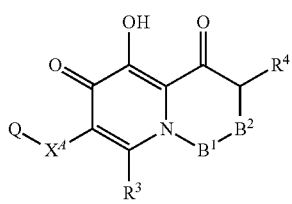

(QI-B-6)

Preferably, $B^1$ is $CR^{20}R^{21}$ and $B^2$ is $NR^{22}$ wherein $R^{20}$, $R^{21}$, and $R^{22}$ are defined the same as above.

Alternatively, preferably, $B^1$ is $NR^{22}$ and $B^2$ is $CR^{20}R^{21}$ wherein $R^{20}$, $R^{21}$, and $R^{22}$ are defined the same as above.

$R^3$ is preferably hydrogen or optionally substituted lower alkyl; and more preferably hydrogen.

$R^{20}$, $R^{21}$ and $R^{22}$ are preferably each independently, hydrogen, optionally substituted lower alkyl (example of substituent: amino, lower alkylamino, lower carbonylamino, lower alkoxy, aryloxy, cyano, halogen, acylamino (e.g., lower carbonylamino), lower alkynyl, hydroxy, lower alkoxycarbonyl, optionally substituted heterocyclylcarbonyl (example of substituent: lower alkyl, lower alkoxy), lower alkenyl, optionally substituted carbamoyl (example of substituent: lower alkyl), lower alkylcarbonyloxy, lower alkyloxycarbonyl, lower alkylcarbonylamino, oxo, lower alkynyl), cycloalkyl, cycloalkyl lower alkyl, optionally substitutedaryl (example of substituent: lower alkyl, halogen, lower alkyloxy, nitro), optionally substituted aryl lower alkyl (example of substituent: lower alkyl, halogen, lower alkyloxy, nitro, oxo), optionally substituted heterocyclic group (example of substituent: lower alkyl, halogen, lower alkyloxy, nitro), optionally substituted heterocyclyl lower alkyl (example of substituent: lower alkyl, halogen, lower alkyloxy, nitro, oxo), optionally substituted lower alkylcarbonyl (substituent: lower alkoxy, halogen), cycloalkyl carbonyl, optionally substituted benzoyl (substituent: lower alkoxy, halogen), or substituted sulfonyl (substituent: lower alkyl, aryl, heterocyclic group (preferably 5- to 6-membered aromatic heterocyclic group)).

More preferably, $R^{20}$ and $R^{21}$ are both hydrogen.

In Compound (QI-B-6), more preferably, $X^4$ is lower alkylene; $R^3$ is hydrogen; $B^1$ is $CH_2$ or $NR^{22}$; $B^2$ is $NR^{22}$ or $CH_2$; and more preferably $B^1$ is $NR^{22}$; and $B^2$ is $CH_2$.

$R^4$ is, preferably, optionally substituted lower alkyl (e.g., methyl, ethyl, n-propyl, i-propyl, n-butyl; example of substituent: hydroxy, amino, lower alkylamino, lower alkoxy, aryloxy, oxo, lower alkoxycarbonyl, optionally substituted heterocyclylcarbonyl (example of substituent: lower alkyl, lower alkoxy)), specifically, lower alkylamino lower alkyl (e.g., 2-dimethylaminoethyl, 2-diethylaminoethyl), lower alkoxy lower alkyl (e.g., 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl) or aryloxy lower alkyl (e.g., 2-phenoxyethyl, 3-phenoxypropyl); optionally substituted cycloalkyl (e.g., cyclopropyl); optionally substituted cycloalkyl lower alkyl (e.g., cyclopropylmethyl, 1-adamantylmethyl, 2-adamantylmethyl, dodecahedranemethyl, cubanemethyl); optionally substituted aryl (e.g., phenyl; example of substituent: lower alkyl, halogen, lower alkyloxy, nitro; or a substituent part may be lower alkylene that may be intervened by a heteroatom (e.g., O)); optionally substituted aryl lower alkyl (e.g., benzyl; example of substituent: lower alkyl, halogen, lower alkyloxy, nitro; or a substituent part may be lower alkylene that may be intervened by a heteroatom (e.g., O)); optionally substituted heterocyclic group (preferably 5- to 6-membered ring) (e.g., picolyl, pyridyl; example of substituent: lower alkyl, halogen, lower alkyloxy, nitro); or optionally substituted heterocyclic group (preferably 5- to 6-membered ring) lower alkyl (e.g., piperonylmethyl, 2-morpholinoethyl, thiophenemethyl, furanmethyl, tetrahydrofuranmethyl, dioxanemethyl, tetrahydropyranmethyl, thiazolemethyl, oxazolemethyl, 1,2,4-oxadiazolemethyl, 1,3,4-oxadiazolemethyl; example of substituent: lower alkyl, halogen, lower alkyloxy, nitro; and the heterocycle may be condensed to a benzene ring).

$R^{22}$ is, preferably, optionally substituted alkyl (e.g., methyl, ethyl, n-propyl, i-propyl, n-butyl, neopentyl; example of substituent: amino, lower alkylamino, lower alkoxy, aryloxy, cyano, halogen, (substituted) carbamoyl, acylamino, oxo), specifically, lower alkylamino lower alkyl (e.g., 2-dimethylaminoethyl, 2-diethylaminoethyl), lower alkoxy lower alkyl (e.g., 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl), aryloxy lower alkyl (e.g., 2-phenoxyethyl, 3-phenoxypropyl), cyano lower alkyl (e.g., cyanomethyl), halogenated lower alkyl (e.g., fluoromethyl, 2,2,2-fluorotrifluoromethyl), or carboranemethyl, acylamino lower alkyl (e.g., 2-acetamidoethyl); lower alkenyl (e.g., allyl, propargyl, crotyl); cycloalkyl lower alkyl (e.g., 3-cyclopropyl, cyclopropylmethyl, 1-adamantylmethyl, 2-adamantylmethyl, dodecahedranemethyl, cubanemethyl); optionally substituted aryl (e.g., phenyl; a substituent part may be lower alkylene that may be intervened by a heteroatom (e.g., O)); optionally substituted aryl lower alkyl (e.g., benzyl; a substituent part may be lower alkylene that may be intervened by a heteroatom (e.g., O)); optionally substituted heterocyclic group (e.g., picolyl, pyridyl; example of substituent: lower alkyl); optionally substituted heterocyclyl lower alkyl (e.g., piperonylmethyl, morpholinoethyl, furanmethyl, tetrahydrofuranmethyl, dioxanemethyl, tetrahydropyranmethyl, triazolemethyl, tetrazolemethyl, thiazolemethyl, oxazolemethyl, 1,2,4-oxadiazolemethyl, 1,3,4-oxadiazolemethyl, isoxazolemethyl, imidazolemethyl, methylpyrrolemethyl, 18-crown ether methyl; example of substituent: lower alkyl); optionally substituted lower alkyl-carbonyl (e.g., acetyl; example of substituent: lower alkoxy (e.g., methoxy)); optionally substituted aryl carbonyl (e.g., benzoyl; example of substituent: lower alkoxy); substituted (thio)urea (e.g., urea, lower alkyl urea (e.g., dimethylurea), dimethylthiourea); or substituted sulfonyl (e.g., alkylsulfonyl (e.g., methanesulfonyl), aryl sulfonyl (e.g., benzenesulfonyl), heterocyclyl sulfonyl (e.g., thiophenesulfonyl))).

[Chemical formula 21]

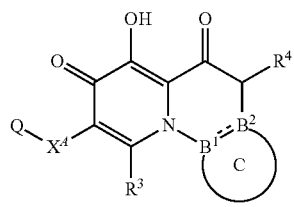

(QI-B-9)

The C ring represents an optionally substituted carbocycle or optionally substituted heterocycle. When the C ring is heterocycle, $B^1$ and $B^2$ are each independently C, CH, or N; with the proviso that when $B^1$ and $B^2$ are each independently $CR^{23}$ or N, the broken line represents the absence of a bond. When the C ring is a heterocycle, examples thereof include the same heterocycle as those of the A ring and the G ring, and examples of a substituent (s) on the C ring similarly include. That is, examples of a substituent (s) on the C ring include the same or different, one or more substituents selected from the foregoing Substituent group S2. Alternatively, a substituent part on the C ring may be taken together with the adjacent atom to further form a condensed ring or spiro ring, preferably, optionally substituted carbocycle (preferably 5- to 6-membered ring) or optionally substituted heterocycle (preferably 5- to 6-membered ring).

When the C ring is carbocycle, $B^1$ and $B^2$ are each independently C or CH. Examples of the carbocycle include 5- to 7-membered ring.

The broken line represents the presence or absence of a bond, and preferably represents the absence.

The C ring encompasses the following rings, and preferably is (i) or (l):

[Chemical formula 22]

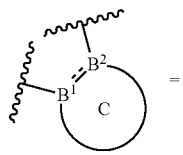

(a) 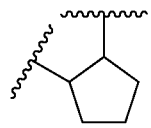

(b) 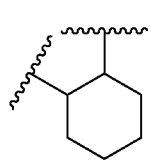

(c) 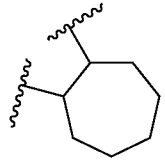

(d) 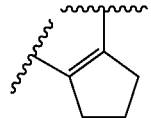

(e) 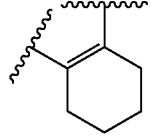

(f) 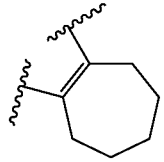

(g) 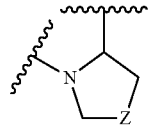

(h) 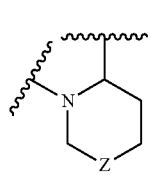

-continued

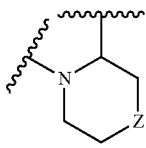 (i)

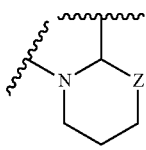 (j)

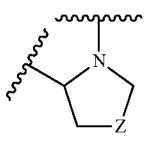 (k)

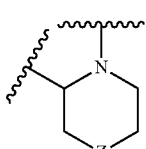 (l)

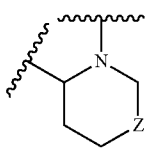 (m)

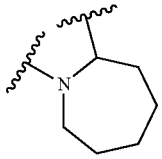 (n)

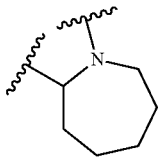 (o)

wherein Z is $CH_2$, O, S, SO, $SO_2$, or $NR^{19}$.

One of preferred embodiments as a substituent (s) on the C ring is lower alkyl (e.g., methyl, isopropyl), lower alkoxy lower alkyl (e.g., 2-methoxyethyl), optionally substituted amino (example of substituent: lower alkyl (e.g., methyl), lower alkylcarbonyl (e.g., acetyl)).

$R^{19}$ is more preferably, hydrogen, lower alkyl, or lower alkoxy lower alkyl.

$R^3$ is preferably hydrogen or optionally substituted lower alkyl, more preferably hydrogen.

In Compound (QI-B-9), examples of $R^4$ include, preferably, the same groups as $R^4$ of Compound (QI-B-6).

[Chemical formula 23]

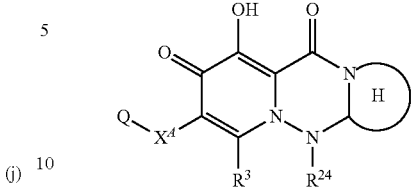 (QI-B-12)

The H ring means the heterocycle defined the same as the A ring, and preferably is a 5- to 7-membered ring. Also, examples of a substituent (s) on each ring include the same substituent as in the case of the A ring. That is, examples of a substituent (s) on the H ring include the same or different, one or more substituents selected from the foregoing Substituent group S2. Alternatively, a substituent part on the H ring may be taken together with the adjacent atom to further form a condensed ring or spiro ring, preferably, optionally substituted carbocycle (preferably 5- to 6-membered ring) or optionally substituted heterocycle (preferably 5- to 6-membered ring).

$R^3$ is preferably hydrogen or optionally substituted lower alkyl; and more preferably hydrogen.

Examples of $R^{24}$ include the same groups as in the case of $R^{20}$, $R^{21}$, $R^{22}$, and $R^{23}$ described above. However, it is preferably hydrogen, optionally substituted lower alkyl (substituent: amino, lower alkylamino, lower alkoxy, aryloxy, cyano, halogen, (substituted) carbamoyl, acylamino, lower alkynyl, hydroxy), cycloalkyl, cycloalkyl lower alkyl, phenyl, benzyl, 5- to 6-membered aromatic heterocyclic group, 5- to 6-membered heterocyclyl lower alkyl, optionally substituted lower alkylcarbonyl (substituent: lower alkoxy, halogen), optionally substituted benzoyl (substituent: lower alkoxy, halogen), or substituted sulfonyl (substituent: lower alkyl, aryl, heterocyclic group (preferably 5- to 6-membered aromatic heterocyclic group)); and more preferably hydrogen or optionally substituted lower alkyl.

Compound (QI) has at least the following characteristics as its chemical structure:

(1) the condensed heterocycle, which is the main backbone, is substituted with oxo (=O), hydroxy (OH), and oxo (=O); and (2) an adjacent position to oxo on the condensed heterocycle has a side chain represented by —$X^4$-Q.

By possession of such a structure, the compound exhibits remarkably potent integrase inhibitory activity and/or cell proliferation inhibitory activity against viruses including HIV. Meanwhile, the structures of other parts ($R^4$, $Z^2$, $R^3$, etc.) can be relatively freely selected from various structures, may have any kind of substituent, may form a condensed ring, and the condensed ring may be further substituted.

The present invention also provides pharmaceutically acceptable salts of Compound (QI), and solvates thereof. All theoretically possible tautomers, geometrical isomers, stereoisomers, optical isomers, racemates, and the like of the present compound are also within the scope of the invention.

Pharmaceutically acceptable salts of a compound of the present invention include, as basic salts, for example, alkali metal salts such as sodium salts, potassium salts, and the like; alkaline-earth metal salts such as calcium salts, magnesium salts, and the like; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts, ethylenediamine salts, and the like; aralkylamine salts such as N,N-dibenzylethylenediamine salts, benethamine salts, and the like; heterocyclic aromatic amine salts such as pyridine salts, picoline salts, quinoline salts, isoquinoline salts, and the like; quaternary ammonium salts such as tetramethylammonium salts, tetraethylammonium salts, benzyltrimethylammonium salts, benzyltriethylammonium salts, benzyltributylammonium salts, methyltrioctylammonium salts, tetrabutylammonium salts, and the like; basic amino acid salts such as arginine salts, lysine salts, and the like; and the like. Acid salts thereof include, for example, inorganic acid salts such as hydrochlorides, sulfates, nitrates, phosphates, carbonates, hydrogen carbonates, and perchlorates, and the like; organic acid salts such as acetates, propionates, lactates, maleates, fumarates, tartrates, malates, citrates, ascorbates, and the like; sulfonates such as methanesulfonates, isethionates, benzenesulfonates, p-toluenesulfonates, and the like; acidic amino acid salts such as aspartates, glutamates, and the like; and the like.

Solvates of a compound of the present invention include solvates with alcohol, hydrates, and the like.

The present compound can be synthesized in accordance with methods described in Patent Documents 10 or 11.

Further, as described in Example 1, the present compound can be synthesized using an amide compound described in Patent Document 10 or 11, preferably a hydroxy-protected compound thereof as a raw material. Specifically, the present compound having any kind of amide-type side chain can be synthesized by hydrolyzing the amide side chain portion of the amide compound according to a well known method in the art to convert to a carboxylic acid, followed by, for example, reacting with any kind of amine reagent to perform an amidation reaction and, if desired, then deprotecting:

[Chemical formula 24]

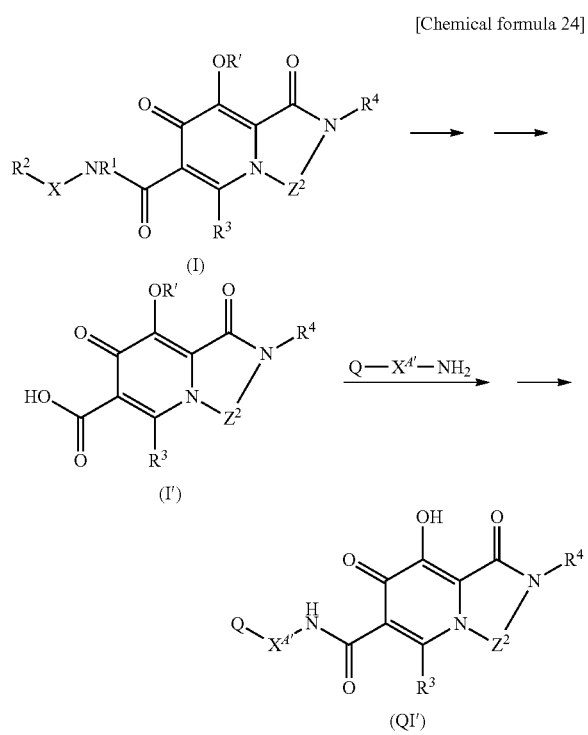

wherein —$X^{A'}$—NH—C(O)— is one example of $X^A$ and other symbols are defined the same as above.

In addition, the present compound obtained above may be further chemically modified to synthesize another compound. Moreover, in the above reaction, when a reactive functional group (e.g., OH, COOH, $NH_2$) is present on a side chain part, etc., the group may be protected before the reaction and may be deprotected after the reaction if desired.

Examples of protecting groups (such as amino protecting group, hydroxy protecting group, and the like) can include protecting groups, such as ethoxycarbonyl, t-butoxycarbonyl, acetyl, benzyl, and the like, which are described in Protective Groups in Organic Synthesis, written by T. W. Greene, John Wiley & Sons Inc. (1991), or the like. Methods for the introduction and removal of a protecting group are methods commonly used in synthetic organic chemistry (see, for example, methods described in Protective Groups in Organic Synthesis, written by T. W. Greene, John Wiley & Sons Inc., (1991), or the like) or can be obtained in accordance therewith. In addition, a functional group included in each substituent can be converted by a known method (for example, those described in Comprehensive Organic Transformations, written by R. C. Larock (1989), and the like) in addition to the above production methods. Some of the compounds of the present invention can be used as a synthetic intermediate, further leading to a new derivative. Intermediates and target compounds produced in each of the above production methods can be isolated and purified by a purification method commonly used in synthetic organic chemistry, for example, subjecting them to neutralization, filtration, extraction, washing, drying, concentration, recrystallization, any kind of chromatography, or the like. In addition, intermediates can be subjected to a next reaction without further purification.

The present compound is useful, for example, as a medicament such as anti-viral agent and the like. The present compound has remarkable inhibitory activity against virus integrase. Therefore, the present compound can be expected to have a preventive or therapeutic effect on various diseases caused by a virus which produces at least integrase and increases at infection in an animal cell; and, for example, it is useful as an integrase inhibiting agent against retroviruses (e.g., HIV-1, HIV-2, HTLV-1, SIV, FIV, etc.); and useful as an anti-HIV agent and the like. A preferred compound also has the following characteristics as pharmacokinetics in the body: the blood concentration is high; the duration of an effect is long; the transitivity to tissue is remarkable; and/or the like. In addition, a preferred compound is safe with regard to a side effect.

In addition, the present compound may be used in a combination therapy in combination with an anti-HIV agent having the different action mechanism such as a reverse transcriptase inhibitor and/or a protease inhibiting agent, etc.

Further, the above use includes not only use as a mixture for anti-HIV, but also use as a concomitant agent for increasing the anti-HIV activity of another anti-HIV agent such as cocktail therapy and the like.

In addition, the present compound can be used to prevent infection with a retrovirus vector from spreading into a tissue other than a target tissue, upon use of a retrovirus vector based on HIV or MLV in the field of gene therapy. Particularly, when a cell or the like is infected with a vector in vitro and then returned into a body, if the present compound is administered in advance, unnecessary infection in the body can be prevented.

The present compound can be administered orally or parenterally. In the case of oral administration, the present compound can be also used as a conventional preparation, for example, as any dosage form of a solid agent such as tablet, powder, granule, capsule, and the like; pharmaceutical solution; oleaginous suspension; liquid such as syrup and elixir; or the like. In the case of parenteral administration, the present compound can be used as an aqueous or oleaginous suspended injection, or a nasal drop. Upon preparation of it any conventional excipients, binders, lubricants, aqueous solvents, oleaginous solvents, emulsifiers, suspending agents, preservatives, stabilizers and the like may be used. In addition, as an anti-HIV agent, an oral agent is particularly preferred. A preparation of the present invention is produced by combining (e.g. mixing) a therapeutically effective amount of the present compound with a pharmaceutically acceptable carrier or diluent.

The dose of a compound of the present invention varies depending on an administration method, the age, weight and condition of a patient, and the type of a disease. Usually, in the case of oral administration, about 0.05 mg to 3000 mg, preferably about 0.1 mg to 1000 mg, may be administered per adult daily, if necessary, by dividing the dose. In addition, in the case of parenteral administration, about 0.01 mg to 1000 mg, preferably about 0.05 mg to 500 mg, is administered per adult daily.

EXAMPLES

Hereinafter, Examples are described. However, the technical scope of the present invention is not limited by the Examples and the like.

<Abbreviation>

Boc: t-Butoxycarbonyl
DMAP: Dimethylaminopyridine
THF: Tetrahydrofuran
HATU: 2-(1H-7-Azabenzotriazol-1-yl)-1,1,3,3-tetramethyluronium hexafluorophosphate methanaminium
TFA: Trifluoroacetic acid
Me: Methyl
Et: Ethyl
Bu: Butyl
Ph: Phenyl
Bn: Benzyl.

Example 1

[Chemical formula 25]

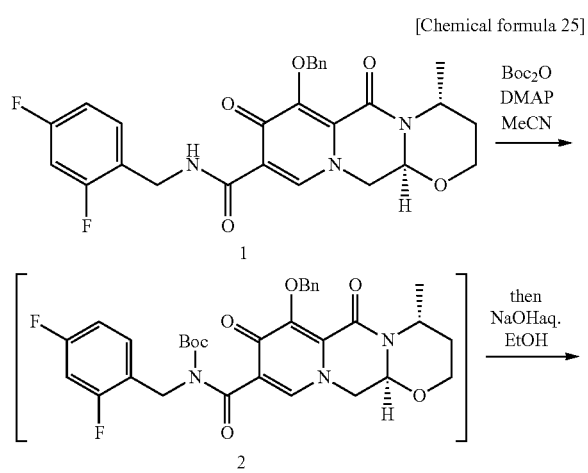

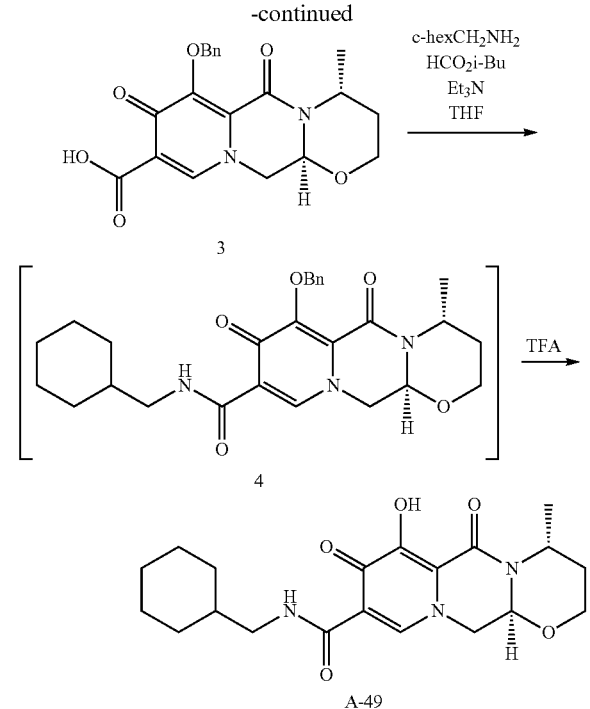

(1) To an acetonitrile solution (80 mL) of amide 1 (8.00 g, 14.5 mmol) was added Boc$_2$O (10.0 g, 45.8 mmol) and DMAP (7.07 g, 57.8 mmol) at room temperature. The reaction mixture was then stirred under heating to 80° C., and Boc$_2$O (10.0 g, 45.8 mmol) was added thereto every 10 minutes. After the raw material disappeared, aqueous 2 N sodium hydroxide solution (578 mL, 1.15 mol) and ethanol (80 mL) were added thereto, the reaction mixture was then stirred under heating to 60° C. for 5 hours. The reaction solution was evaporated off under reduced pressure, and then ethyl acetate was added to the resulting residue, followed by extraction with aqueous saturated sodium hydrogen carbonate solution. After aqueous 2 N hydrochloric acid solution was added to the aqueous layer to acidify it, it was extracted with chloroform, and then the organic layer was dried over sodium sulfate. The solvent was evaporated off under reduced pressure, and then the resulting residue was purified by silica gel column chromatography (chloroform:methanol=95:5). Solidifying from the solution of the resulting residue in a mixture of methylene chloride-diethyl ether yielded carboxylic acid 3 as a white solid (3.58 g, 64%).

$^1$H NMR (CDCl$_3$, 300 MHz) δ 1.35 (d, J=7.1 Hz, 3H), 1.46-1.56 (m, 1H), 2.08-2.24 (m, 1H), 3.95 (d, J=2.5 Hz, 1H), 3.98 (dd, J=3.3, 1.9 Hz, 1H), 4.15 (dd, J=13.5, 5.8 Hz, 1H), 4.28 (dd, J=13.5, 3.8 Hz, 1H), 4.93-5.06 (m, 1H), 5.19 (dd, J=5.8, 3.8 Hz, 1H), 5.37 (d, J=10.2 Hz, 1H), 5.42 (d, J=10.2 Hz, 1H), 7.28-7.40 (m, 3H), 7.56-7.62 (m, 2H), 8.32 (s, 1H); ESI-MS [M+H$^+$] calculated: 385, observed: 385.

(2) To a THF solution (3 mL) of carboxylic acid 3 (150 mg, 0.390 mmol) was added triethylamine (162 μL, 1.17 mmol) at room temperature, and then the reaction mixture was stirred for 10 minutes. Under cooling (−15° C.), isobutyl chloroformate (154 μL, 1.17 mmol) was slowly added dropwise thereto, followed by stirring for 50 minutes. After cyclohexylmethylamine (508 μL, 3.90 mmol) was added, the reaction mixture was stirred for 3 hours while allowing it to slowly warm to room temperature. Water was added to the reaction solution, followed by extraction with ethyl acetate. The organic layer was washed with aqueous saturated ammonium chloride solution and water, and then dried over sodium sulfate. The solvent was evaporated off under reduced pressure, and then the resulting residue was purified by silica gel column chromatography (chloroform:methanol=98:2). The resulting white solid was dissolved in THF-methanol solution (1:1, 2 mL), and then palladium on carbon (18.0 mg, 0.0170 mmol) was added thereto, followed by stirring at room temperature under hydrogen atmosphere for 2 hours. After the reaction solution was filtered through celite, the solvent was evaporated off under reduced pressure, and then the resulting residue was purified by high performance liquid chromatography (0.3% formic acid in acetonitrile:0.3% formic acid in water=20:80-50:50/5 minutes) to yield the target compound A-49 as a white solid (106 mg, 70%).

$^1$H NMR (CDCl$_3$, 300 MHz) δ 0.90-1.32 (m, 5H), 1.45 (d, J=6.9 Hz, 3H), 1.49-1.85 (m, 7H), 2.15-2.32 (m, 1H), 3.26-3.32 (m, 2H), 4.02 (d, J=2.1 Hz, 1H), 4.03-4.07 (m, 1H), 4.12 (dd, J=13.4, 5.9 Hz, 1H), 4.27 (dd, J=13.4, 3.8 Hz, 1H), 4.94-5.06 (m, 1H), 5.26 (dd, J=5.9, 3.8 Hz, 1H), 8.29 (s, 1H), 10.00-10.11 (m, 1H), 12.39 (s, 1H); ESI-MS [M+H$^+$] calculated: 390, observed: 390.

Example 2

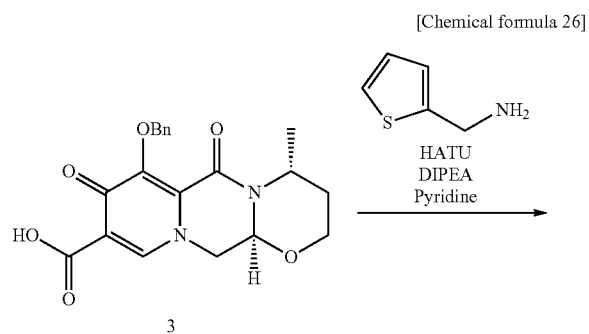

[Chemical formula 26]

To a pyridine solution (400 μL) of carboxylic acid 3 (20 mg, 0.052 mmol) and HATU (30 mg, 0.079 mmol) was added di-isopropylethylamine (DIPEA) (36 μL, 0.21 mmol) at room temperature, and then the reaction mixture was stirred for 10 minutes. After 2-aminomethylthiophene (5.9 mg, 0.052 mmol) was added to the reaction solution, it was stirred at room temperature for 5 hours. A chloroform-methanol (9:1) solution and an aqueous sodium hydrogen carbonate solution were added to the reaction solution, and then the organic layer and the aqueous layer were separated. The aqueous layer was washed with chloroform-methanol (9:1) solution, and then the combined organic layer was evaporated off under reduced pressure. TFA (400 μL) was added to the resulting residue, followed by stirring at room temperature for 5 hours. The reaction solution was evaporated off under reduced pressure, and then the resulting residue was purified by high performance liquid chromatography to yield the target compound A-39 as a yellow solid (4.4 mg, 22%). ESI-MS [M+H$^+$] calculated: 390, observed: 390.

Example 3

Specific compounds and physical property data (MS) thereof are described below.

TABLE 1-1

| Compound No. | Structural formula | ESI-MS [M + H+] |
|---|---|---|
| A-2 | | 458 |

TABLE 1-1-continued

| Compound No. | Structural formula | ESI-MS [M + H+] |
|---|---|---|
| A-3 | | 402 |
| A-4 | | 376 |
| A-5 | | 413 |

TABLE 1-2

| Compound No. | Structural formula | ESI-MS [M + H+] |
|---|---|---|
| A-6 | | 407 |
| A-7 | | 386 |
| A-8 | | 397 |

TABLE 1-2-continued

| Compound No. | Structural formula | ESI-MS [M + H+] |
|---|---|---|
| A-10 | | 391 |

TABLE 1-3

| Compound No. | Structural formula | ESI-MS [M + H+] |
|---|---|---|
| A-11 | | 421 |
| A-12 | | 391 |
| A-13 | | 385 |
| A-14 | | 445 |

TABLE 1-4

| Compound No. | Structural formula | ESI-MS [M + H+] |
| --- | --- | --- |
| A-15 | | 460 |
| A-16 | | 422 |
| A-18 | | 454 |
| A-19 | | 376 |

TABLE 1-5

| Compound No. | Structural formula | ESI-MS [M + H+] |
| --- | --- | --- |
| A-20 | | 440 |

TABLE 1-5-continued

| Compound No. | Structural formula | ESI-MS [M + H+] |
|---|---|---|
| A-21 | | 378 |
| A-22 | | 385 |
| A-23 | | 441 |

TABLE 1-6

| Compound No. | Structural formula | ESI-MS [M + H+] |
|---|---|---|
| A-24 | | 377 |
| A-25 | | 427 |
| A-26 | | 453 |

TABLE 1-6-continued
| Compound No. | Structural formula | ESI-MS [M + H+] |
|---|---|---|
| A-27 | 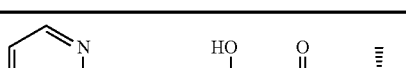 | 386 |
TABLE 1-7
| Compound No. | Structural formula | ESI-MS [M + H+] |
|---|---|---|
| A-28 | | 427 |
| A-29 | | 391 |
| A-30 | | 372 |
| A-31 | | 410 |
TABLE 1-8
| Compound No. | Structural formula | ESI-MS [M + H+] |
|---|---|---|
| A-33 | | 386 |
| A-36 | 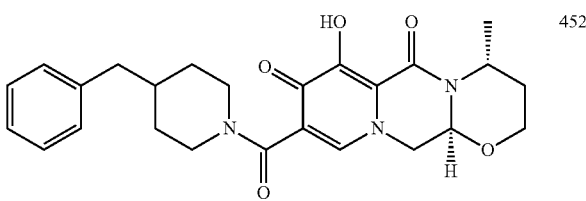 | 452 |

TABLE 1-8-continued

| Compound No. | Structural formula | ESI-MS [M + H+] |
|---|---|---|
| A-37 | (structure) | 421 |
| A-38 | (structure) | 431 |

TABLE 1-9

| Compound No. | Structural formula | ESI-MS [M + H+] |
|---|---|---|
| A-39 | (structure) | 390 |
| A-40 | (structure) | 474 |
| A-41 | (structure) | 374 |
| A-42 | (structure) | 404 |

TABLE 1-10

| Compound No. | Structural formula | ESI-MS [M + H+] |
|---|---|---|
| A-43 | (structure) | 437 |

TABLE 1-10-continued

| Compound No. | Structural formula | ESI-MS [M + H+] |
|---|---|---|
| A-44 | | 423 |
| A-45 | | 435 |
| A-46 | | 378 |

TABLE 1-11

| Compound No. | Structural formula | ESI-MS [M + H+] |
|---|---|---|
| A-47 | | 399 |
| A-48 | | 413 |
| A-49 | | 389 |

TABLE 1-11-continued

| Compound No. | Structural formula | ESI-MS [M + H+] |
|---|---|---|
| A-50 | | 404 |

TABLE 1-12

| Compound No. | Structural formula | ESI-MS [M + H+] |
|---|---|---|
| A-51 | | 475 |

TABLE 1-12-continued

| Compound No. | Structural formula | ESI-MS [M + H+] |
|---|---|---|
| A52 | | 419 |
| A-53 | | 424 |
| A-54 | | 411 |

TABLE 1-13

| Compound No | Structural formula | ESI-MS [M + H+] |
|---|---|---|
| A-55 | | 426 |
| A-56 | | 390 |
| A-57 | | 396 |

TABLE 1-13-continued

| Compound No | Structural formula | ESI-MS [M + H+] |
|---|---|---|
| A-58 | | 424 |
| A-59 | | 385 |

TABLE 1-14

| Compound No. | Structural formula | ESI-MS [M + H+] |
|---|---|---|
| A-62 | | 436 |
| A-63 | | 419 |
| A-65 | | 404 |
| A-66 | | 441 |

TABLE 1-15
| Compound No. | Structural formula | ESI-MS [M + H+] |
|---|---|---|
| A-67 | 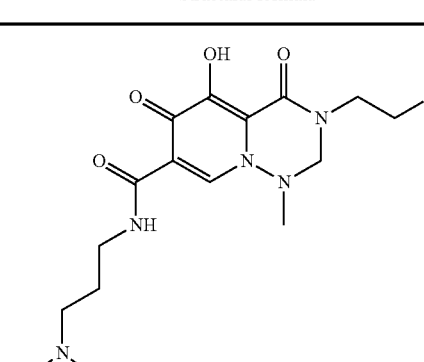 | 464 |
Example 4
Specific compounds are described below.
TABLE 2-1
| Compound No. | Structural formula |
|---|---|
| B-1 | 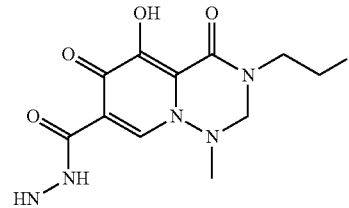 |
| B-2 | 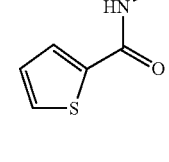 |
| B-3 | 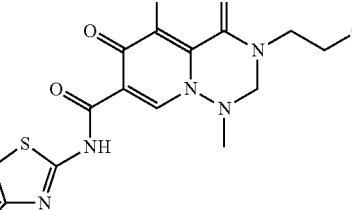 |
TABLE 2-1-continued
| Compound No. | Structural formula |
|---|---|
| B-6 | 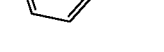 |
TABLE 2-2
| Compound No. | Structural formula |
|---|---|
| B-7 | 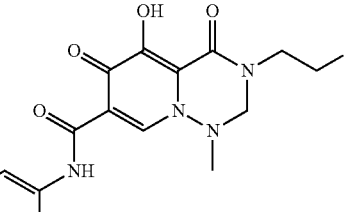 |
| B-8 | 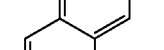 |
| B-9 |  |

TABLE 2-2-continued

| Compound No. | Structural formula |
|---|---|
| B-11 | (structure: core bicyclic system with OH, =O, N-methyl, N-CH2CH2OCH3, and C(=O)NH-(2-phenylphenyl)) |

TABLE 2-3

| Compound No. | Structural formula |
|---|---|
| B-12 | (structure: core bicyclic system with C(=O)NH-quinolin-8-yl substituent) |
| B-13 | (structure: core bicyclic system with C(=O)NH-cyclohexyl substituent) |
| B-14 | (structure: core bicyclic system with C(=O)NH-NH-C(=O)-phenyl substituent) |

TABLE 2-3-continued

| Compound No. | Structural formula |
|---|---|
| B-15 | (structure: core bicyclic system with C(=O)NH-CH2CH2-(2-thienyl) substituent) |

TABLE 2-4

| Compound No. | Structural formula |
|---|---|
| B-16 | (structure: core bicyclic system with C(=O)NH-CH2CH2-O-phenyl substituent) |
| B-17 | (structure: core bicyclic system with C(=O)NH-CH2-(pyridin-2-yl) substituent) |
| B-18 | (structure: core bicyclic system with C(=O)NH-CH2-CH(phenyl)2 substituent) |

TABLE 2-4-continued

| Compound No. | Structural formula |
|---|---|
| B-19 | (structure: bicyclic pyridazine-triazine core with OH, two C=O, N-CH2CH2-OCH3, N-CH3, and C(=O)NH-CH2CH2-cyclohexenyl) |

TABLE 2-5

| Compound No. | Structural formula |
|---|---|
| B-20 | (structure: same bicyclic core with C(=O)NH-CH2-(pyridin-4-yl)) |
| B-21 | (structure: same bicyclic core with C(=O)NH-CH2CH2-(pyridin-3-yl)) |
| B-22 | (structure: same bicyclic core with C(=O)NH-CH2-(pyridin-3-yl)) |

TABLE 2-5-continued

| Compound No. | Structural formula |
|---|---|
| B-23 | (structure: same bicyclic core with C(=O)NH-CH2CH2-piperidin-1-yl) |

TABLE 2-6

| Compound No. | Structural formula |
|---|---|
| B-24 | (structure: same bicyclic core with C(=O)NH-CH2CH2-morpholin-4-yl) |
| B-25 | (structure: same bicyclic core with C(=O)NH-CH2CH2CH2-phenyl/cyclohexadienyl) |

TABLE 2-6-continued
| Compound No. | Structural formula |
|---|---|
| B-26 | 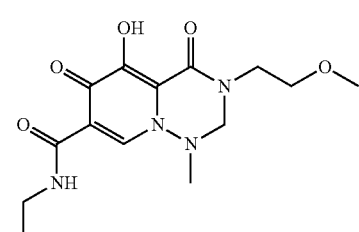 |
| B-27 | 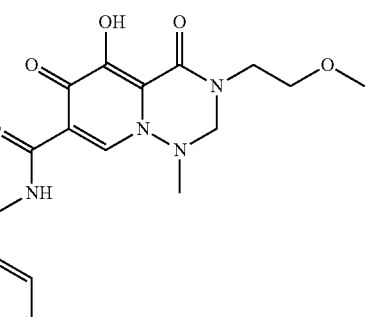 |
TABLE 2-7
| Compound No. | Structural formula |
|---|---|
| B-31 | 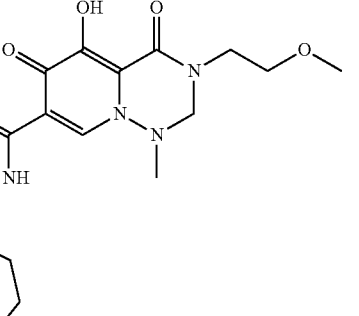 |
TABLE 2-7-continued
| Compound No. | Structural formula |
|---|---|
| B-32 | 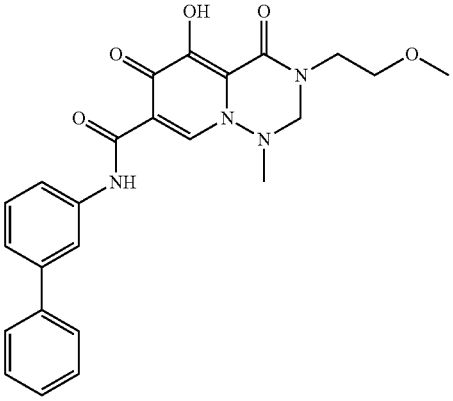 [SMILES: COCCN1CN(C)n2cc(C(=O)Nc3cccc(-c4ccccc4)c3)c(=O)c(O)c2C1=O] |
| B-34 | 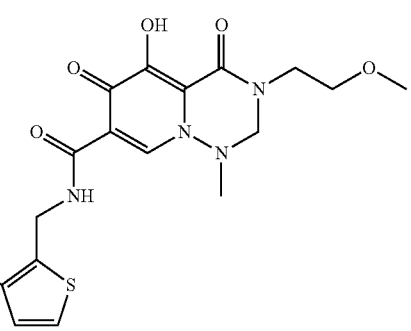 |
| B-36 | 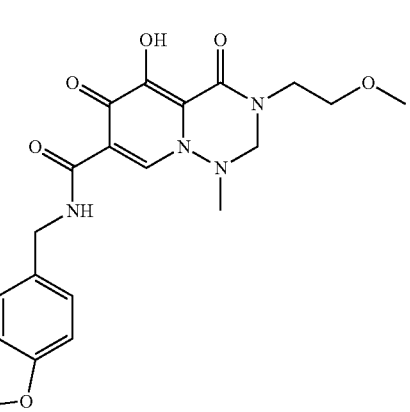 |

TABLE 2-8

| Compound No. | Structural formula |
|---|---|
| B-37 | |
| B-38 | |
| B-39 | |
| B-40 | |

TABLE 2-9

| Compound No. | Structural formula |
|---|---|
| B-41 | |
| B-42 | |
| B-43 | |
| B-44 | |

TABLE 2-10

| Compound No. | Structural formula |
|---|---|
| B-45 | (structure) |
| B-46 | (structure) |
| B-47 | (structure) |
| B-48 | (structure) |

TABLE 2-11

| Compound No. | Structural formula |
|---|---|
| B-49 | (structure) |
| B-50 | (structure) |
| B-51 | (structure) |

TABLE 2-12

| Compound No. | Structural formula |
| --- | --- |
| B-53 | |
| B-54 | |
| B-55 | |
| B-56 | |

TABLE 2-13

| Compound No. | Structural formula |
| --- | --- |
| B-57 | (structure) |
| B-58 | (structure) |
| B-59 | (structure) |
| B-60 | (structure) |

TABLE 2-14

| Compound No. | Structural formula |
| --- | --- |
| B-61 | (structure) |
| B-62 | (structure) |
| B-63 | (structure) |
| B-64 | (structure) |

TABLE 2-15
| Compound No. | Structural formula |
|---|---|
| B-65 | 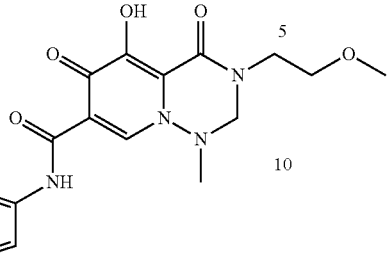 |
| B-66 | 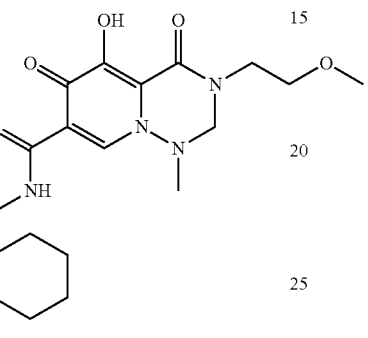 |
| B-67 | 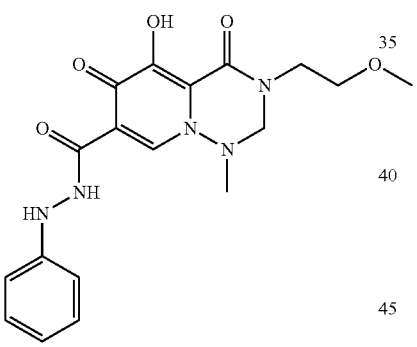 [SMILES: COCCN1CN(C)n2cc(C(=O)NNc3ccccc3)c(=O)c(O)c2C1=O] |
| B-68 | 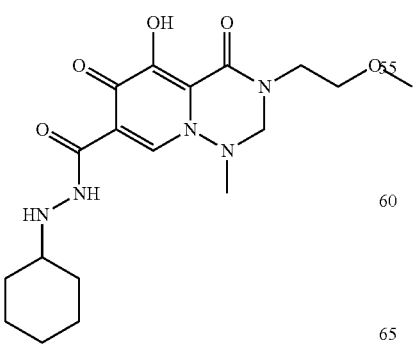 [SMILES: COCCN1CN(C)n2cc(C(=O)NNC3CCCCC3)c(=O)c(O)c2C1=O] |

TABLE 2-16
| Compound No. | Structural formula |
|---|---|
| B-69 | 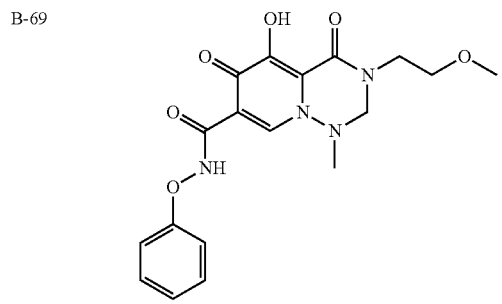 |
| B-70 | 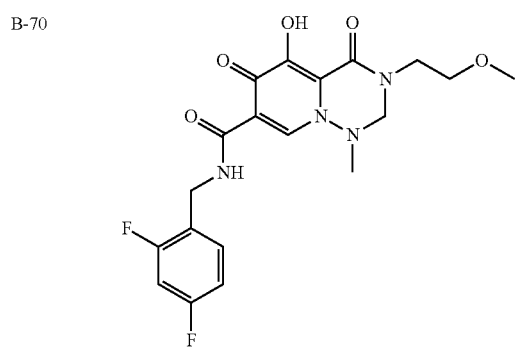 |
| B-71 | 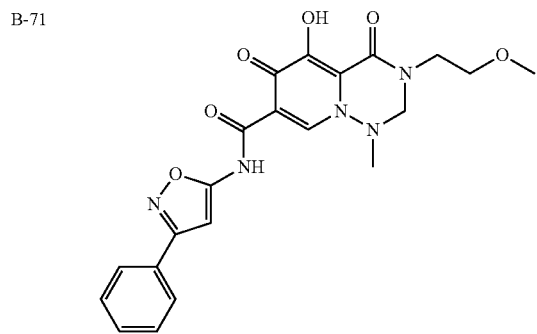 |
| B-72 | 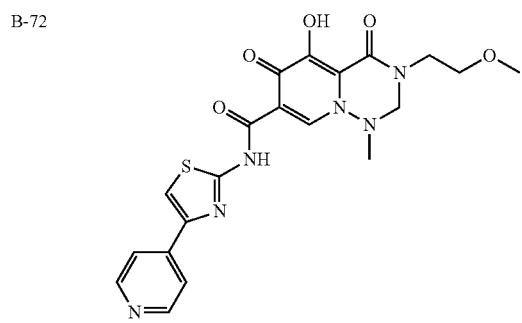 |
TABLE 2-17
| Compound No. | Structural formula |
|---|---|
| B-73 | 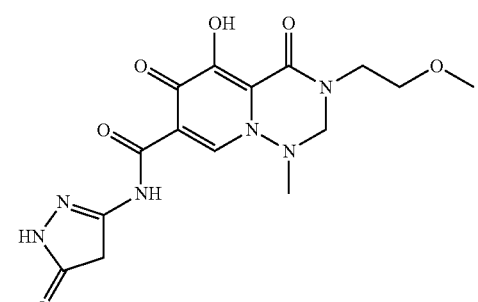 |
| B-75 | 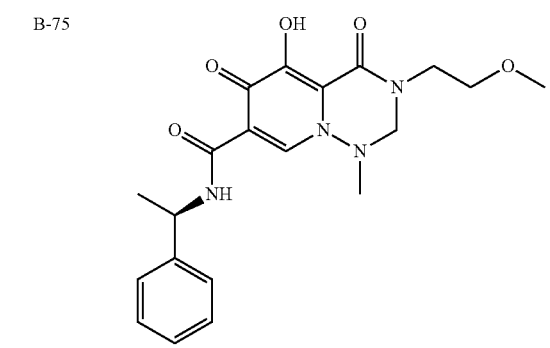 |
| B-76 | 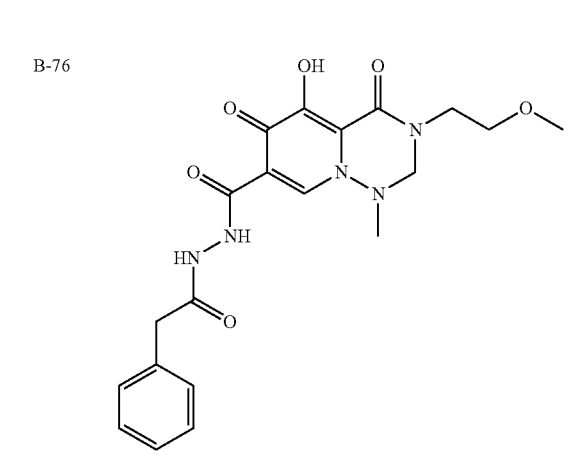 |
| B-77 | 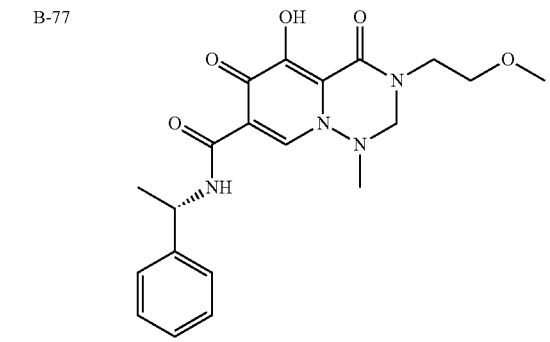 |

TABLE 2-18

| Compound No. | Structural formula |
|---|---|
| B-78 | (structure) |
| B-79 | (structure) |
| B-80 | (structure) |
| B-81 | (structure) |

TABLE 2-19

| Compound No. | Structural formula |
|---|---|
| B-82 | (structure) |
| B-83 | (structure) |
| B-84 | (structure) |
| B-85 | (structure) |

TABLE 2-20

| Compound No. | Structural formula |
|---|---|
| B-86 | (structure) |
| B-87 | (structure) |
| B-88 | (structure) |
| B-89 | (structure) |

TABLE 2-21

| Compound No. | Structural formula |
|---|---|
| B-90 | (structure) |
| B-91 | (structure) |
| B-92 | (structure) |
| B-93 | (structure) |

TABLE 2-22
| Compound No. | Structural formula |
|---|---|
| B-94 | 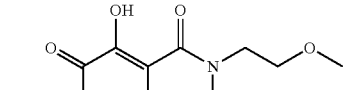 |
| B-95 | 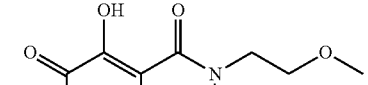 |
| B-97 | 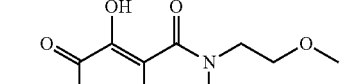 |
| B-98 | 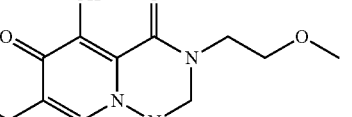 |
TABLE 2-23
| Compound No. | Structural formula |
|---|---|
| B-99 | 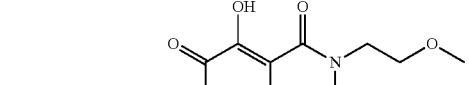 |
| B-100 | 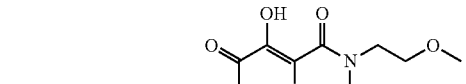 |
| B-101 | 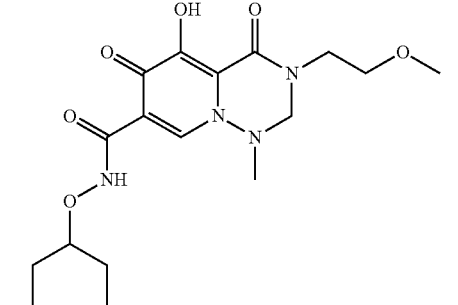 |
| B-102 | 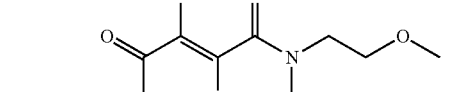 |

TABLE 2-24

| Compound No. | Structural formula |
|---|---|
| B-103 | (structure) |
| B-104 | (structure) |
| B-105 | (structure) |
| B-106 | (structure) |

TABLE 2-25

| Compound No. | Structural formula |
|---|---|
| B-107 | (structure) |
| B-108 | (structure) |
| B-109 | (structure) |
| B-110 | (structure) |

Experimental Example 1

Integrase Inhibitory Activity (Test Method)
(1) Preparation of DNA Solution
By the same method as that described in Experimental Example 1 of Patent Document 2, a substrate DNA solution (2

µmol/µl) and a target DNA solution (5 µmol/µl) were prepared. After each target DNA solution was once boiled, a temperature was slowly lowered to anneal complementary strands, which was then used. Each sequence of a substrate DNA and a target DNA is as described in the same Experimental Example.

(2) Measurement of Inhibition Rate ($IC_{50}$ Value)

Onto Immobilizer—Streptavidin Plates (manufactured by NUNC) was added 50 µl of a substrate DNA solution (2 µmol/µl). After adsorbing at room temperature for 60 minutes under shaking, it was washed with a phosphate buffer two times.

Then, to each well prepared as described above were added 12 µl of a buffer (composition: 150 mM MOPS (pH7.2), 75 mM $MnCl_2$, 50 mM 2-mercaptoethanol, 25% glycerol, 500 µg/ml bovine serum albumin-fraction V), and 51 µl of a reaction solution prepared from 39 µl of distilled water. Then, 9 µl of an integrase solution (30 µmol) was added, and the mixture was mixed well. To a well as a negative control (NC) was added 9 µl of a diluting solution (composition: 20 mM MOPS (pH 7.2), 400 mM potassium glutamate, 1 mM EDTA, 0.1% NP-40, 20% glycerol, 1 mM DTT, 4 M urea), and this was mixed well using a plate mixer.

After the plate was incubated at 30° C. for 60 minutes, the reaction solution was discarded, followed by washing with 200 µl of a washing buffer (composition: 150 mM MOPS (pH 7.2), 50 mM 2-mercaptoethanol, 25% glycerol, 500 µg/ml bovine serum albumin-fraction V) three times.

Then, to each well were added 12 µl of a buffer (composition: 150 mM MOPS (pH 7.2), 75 mM $MgCl_2$, 50 mM 2-mercaptoethanol, 25% glycerol, 500 µg/ml bovine serum albumin-fraction V), and 53 µl of a reaction solution prepared from 41 µl of distilled water. Further, 6 µl of a solution of a test compound in DMSO was added to each well, and 6 µl of DMSO was added to a well as a positive control (PC), followed by mixing well using a plate mixer. After the plate was incubated at 30° C. for 60 minutes, 1 µl of a target DNA (5 µmol/µl) was added, and this was mixed well using a plate mixer.

After each plate was incubated at 30° C. for 10 minutes, the reaction solution was discarded, followed by washing with a phosphate buffer two times. Then, an anti-digoxigenin antibody labeled with alkaline phosphatase (sheep Fab fragment: manufactured by Boehringer) was diluted 2000-fold with an antibody diluting solution, 100 µl of the diluent was added to bind at 30° C. for 1 hour, and this was washed successively with a phosphate buffer containing 0.05% Tween 20 two times, and a phosphate buffer two times. Then, 150 µl of an alkaline phosphatase coloring buffer (composition: 0.9 mM para-nitrophenyl phosphate (manufactured by PIERCE), 1 mM $MgCl_2$, 1M diethanolamine (pH 9.8)) was added to react at 30° C. for 1 hour, an absorbance (OD 405 nm) of each well was measured, and an inhibition rate ($IC_{50}$) was obtained according to the following calculation equation.

Inhibition rate (%)=100[1−{(C abs.−NC abs.)/(PC abs.−NC abs.)}]

C abs.: Absorbance of well of compound

NC abs.: Absorbance of NC

PC abs.: Absorbance of PC (Result)

TABLE 3

| Compound No. | $IC_{50}$ (nM) |
|---|---|
| A-20 | 28.4 |
| A-39 | 27.0 |
| A-50 | 13.5 |
| A-56 | 29.7 |

Experimental Example 2

Anti-HIV Activity (Test Method)

A HeLa-CD4 cell suspension ($2.5 \times 10^4$ cell/well) was dispensed to each well on an assay plate. After incubating at 37° C. for 1 hour under condition of 5% $CO_2$, a solution to dilute a compound (50 µL) was added to each well (provided that a cell control was excluded). A culture solution (50 µL) was added to a well of the cell control. The plate was incubated at 37° C. for 3 days under condition of 5% $CO_2$.

After the culture solution was aspirated from each well, 100 µL of a cell lysate of the reporter assay kit—β gal—was added to all wells, and then the plate was frozen at −80° C. to completely lyse cells. The plate was left at room temperature to unfreeze the cell lysate, it was centrifuged at 1200 rpm for 5 minutes at room temperature (Kubota centrifuge KR-600P). 20 µL of the supernatant was dispensed from each well to 96-well black plate, 100 µL of a luminescent reagent of the reporter assay kit—β gal—was added to each well. The plate was incubated at room temperature for 1 hour. The luminescence intensity from each well was measured by MicroBeta TRILUX instrument (PerkinElmer). A concentration (conc.) to inhibit HIV infection by 50% was calculated to obtain an $EC_{50}$ value.

(Result)

TABLE 4

| Compound No. | $EC_{50}$ (nM) |
|---|---|
| A-12 | 32 |
| A-15 | 16 |
| A-20 | 11 |
| A-21 | 25 |
| A-38 | 15 |
| A-39 | 11 |
| A-41 | 42 |
| A-42 | 46 |
| A-50 | 32 |
| A-56 | 6.4 |
| A-65 | 22 |
| A-66 | 38 |

Formulation Example

A term "active ingredient" means the present compound, a tautomer thereof, a pharmaceutically acceptable salt thereof, or a solvate thereof.

Formulation Example 1

A hard gelatin capsule is prepared using the following ingredients:

|  | Dose (mg/capsule) |
| --- | --- |
| Active ingredient | 250 |
| Starch (dried) | 200 |
| Magnesium stearate | 10 |
| Total | 460 mg |

Formulation Example 2

A tablet is prepared using the following ingredients:

|  | Dose (mg/capsule) |
| --- | --- |
| Active ingredient | 250 |
| Cellulose (microcrystalline) | 400 |
| Silicon dioxide (fumed) | 10 |
| Stearic acid | 5 |
| Total | 665 mg |

Ingredients are mixed, and compressed to obtain tablets, each weighing 665 mg.

The present invention has been exemplified so far by referring to preferable embodiments of the present invention, but it should not be construed that the present invention is restricted by the embodiments of the present invention. It should be understood that the scope of the present invention should be construed only by the claims. It would be understood that those skilled in the art can perform an invention practically equivalent to the present invention, based on the description of the present invention and technical common sense from the specific description of preferable embodiments of the present invention. It would be understood that the patents, patent applications and literature cited herein should be incorporated herein by reference to the present specification in their entire contents, similarly to the case where the contents themselves are described specifically herein.

INDUSTRIAL APPLICABILITY

The present compound has integrase inhibitory activity and/or cell proliferation inhibitory activity against viruses, in particular, HIV. Thus, the compound is useful in preventing or treating various diseases, viral infections (e.g., AIDS), and the like in which integrase participates.

The invention claimed is:
1. A compound represented by the formula QI:

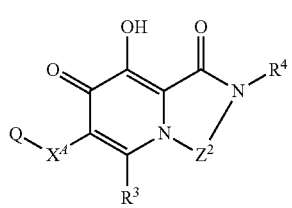

(QI)

wherein
$R^4$ is hydrogen, optionally substituted lower alkyl (with the proviso that the substituent is not optionally substituted aryl), optionally substituted cycloalkyl, optionally substituted cycloalkyl lower alkyl, optionally substituted lower alkenyl, optionally substituted lower alkoxy, optionally substituted aryl, optionally substituted aryloxy, optionally substituted heterocyclic group, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, $NR^a$ (wherein $R^a$ is hydrogen or lower alkyl), —N=, and =N—);
$Z^2$ is optionally substituted lower alkylene or optionally substituted lower alkenylene, wherein said lower alkylene or said lower alkenylene is intervened by a heteroatom group selected from the group consisting of O, S, SO, $SO_2$, and $NR^5$ (wherein $R^5$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, and $NR^5$ (wherein $R^5$ is, independent of $R^4$, selected from the same substituent group as $R^4$), —N=, and =N—));
$X^A$ is a group selected from the following group:
$X^{41}$: a single bond;
$X^{42}$: a group selected from C=O and C=S;
$X^{43}$: a heteroatom group selected from O, S, SO, $SO_2$, and $NR^{1'}$ wherein $R^{1'}$ is hydrogen or lower alkyl,
$X^{44}$: a group formed by linking the same or different, two or more groups selected from $X^{42}$ and $X^{43}$,
$X^{45}$: a group selected from —N=N—, —C(R$^{1'}$)=N—, or —N=C(R$^{1'}$)— wherein $R^{1'}$ is hydrogen or lower alkyl;
$X^{46}$: optionally substituted lower alkylene or optionally substituted lower alkenylene,
$X^{47}$: $X^{46}$ intervened by one or any two or more groups selected from $X^{42}$, $X^{43}$, $X^{44}$, and $X^{45}$; and
$X^{48}$: a spacer consisting of any combination of $X^{41}$ to $X^{47}$;
Q is a group selected from the following group:
$Q^1$: a carbocyclic group that may be substituted and may be condensed; and Q²: a heterocyclic group that may be substituted and may be condensed, with the proviso that the case where —X^A-Q is —CONR¹—X—R² (wherein R¹ is hydrogen or lower alkyl, X is a single bond; a heteroatom group selected from O, S, SO, SO₂, and NH; or lower alkylene or lower alkenylene that may be intervened by the heteroatom group, and R² is optionally substituted aryl)

is excluded;

R³ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino;

or a pharmaceutically acceptable salt thereof, or a solvate thereof.

2. A compound renresented by the formula QI-1:

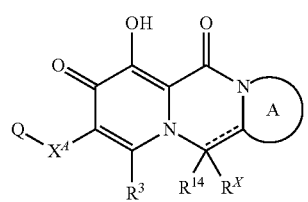

(QI-1)

wherein the A ring is an optionally substituted heterocycle; $R^{14}$ and $R^X$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (wherein the lower alkyl may be intervened by a heteroatom group selected from the group consisting of O, S, SO, SO₂, NR⁵, —N═, and ═N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyloxycarbonyl, or optionally substituted aminocarbonyl; the broken line represents the presence or absence of a bond;

with the proviso that when the broken line represents the presence of a bond, $R^X$ is not present;

$X^A$ is a group selected from the following group:

$X^{A1}$: a single bond;

$X^{A2}$: a group selected from C═O and C═S;

$X^{A3}$: a heteroatom group selected from O, S, SO, SO₂, and NR¹' wherein R¹' is hydrogen or lower alkyl, $X^{A4}$: a group formed by linking the same or different, two or more groups selected from $X^{A2}$ and $X^{A3}$, $X^{A5}$: a group selected from —N═N—, —C(R¹')═N—, or —N═C(R¹')— wherein R¹' is hydrogen or lower alkyl;

$X^{A6}$: optionally substituted lower alkylene or optionally substituted lower alkenylene, $X^{A7}$: $X^{A6}$ intervened by one or any two or more groups selected from $X^{A2}$, $X^{A3}$, $X^{A4}$, and $X^{A5}$; and $X^{A8}$: a spacer consisting of any combination of $X^{A1}$ to $X^{A7}$;

Q is a group selected from the following group:

Q¹: a carbocyclic group that may be substituted and may be condensed; and

Q²: a heterocyclic group that may be substituted and may be condensed, with the proviso that the case where —X^A-Q is —CONR¹—X—R² (wherein R¹ is hydrogen or lower alkyl, X is a single bond; a heteroatom group selected from O, S, SO, SO₂, and NH; or lower alkylene or lower alkenylene that may be intervened by the heteroatom group, and R² is optionally substituted aryl)

is excluded;

R³ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino;

R⁵ is hydrogen, optionally substituted lower alkyl (with the proviso that the substituent is not optionally substituted aryl), optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, SO₂, NR^a (wherein R^a is hydrogen or lower alkyl), —N═, and ═N—);

or a pharmaceutically acceptable salt thereof, or a solvate thereof.

3. A compound represented by the formula QI-11:

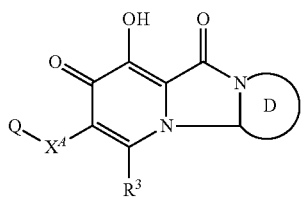

(QI-11)

wherein
the D ring is an optionally substituted heterocycle;
$X^A$ is a group selected from the following group:
$X^{A1}$: a single bond;
$X^{A2}$: a group selected from C=O and C=S;
$X^{A3}$: a heteroatom group selected from O, S, SO, SO$_2$, and NR$^{1'}$ wherein R$^{1'}$ is hydrogen or lower alkyl,
$X^{A4}$: a group formed by linking the same or different, two or more groups selected from $X^{A2}$ and $X^{A3}$,
$X^{A5}$: a group selected from —N=N—, —C(R$^{1'}$)=N—, or —N=C(R$^{1'}$)— wherein R$^{1'}$ is hydrogen or lower alkyl;
$X^{A6}$: optionally substituted lower alkylene or optionally substituted lower alkenylene,
$X^{A7}$: $X^{A6}$ intervened by one or any two or more groups selected from $X^{A2}$, $X^{A3}$, $X^{A4}$, and $X^{A5}$; and
$X^{A8}$: a spacer consisting of any combination of $X^{A1}$ to $X^{A7}$;
Q is a group selected from the following group:
$Q^1$: a carbocyclic group that may be substituted and may be condensed; and
$Q^2$: a heterocyclic group that may be substituted and may be condensed,
with the proviso that the case where —$X^A$-Q is —CONR$^1$—X—R$^2$ (wherein
R$^1$ is hydrogen or lower alkyl,
X is a single bond; a heteroatom group selected from O, S, SO, SO$_2$, and NH; or lower alkylene or lower alkenylene that may be intervened by the heteroatom group, and
R$^2$ is optionally substituted aryl)
is excluded;
R$^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino;
or a pharmaceutically acceptable salt thereof, or a solvate thereof.

4. A compound represented by the formula QI-B:

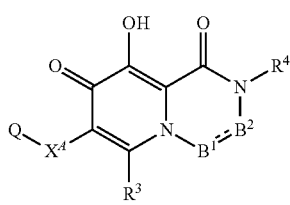

(QI-B)

wherein
the broken line represents the presence or absence of a bond;
either one of B$^1$ and B$^2$ is CR$^{20}$R$^{21}$ and the other is NR$^{22}$, and in this case, the broken line is not present; or
B$^1$ and B$^2$ are each independently C, CR$^{23}$, or N;
R$^{20}$, R$^{21}$, R$^{22}$, and R$^{23}$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (wherein the lower alkyl may be intervened by a heteroatom group selected from the group consisting of O, S, SO, SO$_2$, NR$^5$ (wherein R$^5$ is, independent of R$^4$, selected from the same substituent group as R$^4$), —N=, and =N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl;

$X^A$ is a group selected from the following group:
$X^{A1}$: a single bond;
$X^{A2}$: a group selected from C=O and C=S;
$X^{A3}$: a heteroatom group selected from O, S, SO, SO$_2$, and NR$^{1'}$ wherein R$^{1'}$ is hydrogen or lower alkyl,
$X^{A4}$: a group formed by linking the same or different, two or more groups selected from $X^{A2}$ and $X^{A3}$,
$X^{A5}$: a group selected from —N=N—, —C(R$^{1'}$)=N—, or —N=C(R$^{1'}$)— wherein R$^{1'}$ is hydrogen or lower alkyl;
$X^{A6}$: optionally substituted lower alkylene or optionally substituted lower alkenylene,
$X^{A7}$: $X^{A6}$ intervened by one or any two or more groups selected from $X^{A2}$, $X^{A3}$, $X^{A4}$, and $X^{A5}$; and
$X^{A8}$: a spacer consisting of any combination of $X^{A1}$ to $X^{A7}$;
Q is a group selected from the following group:
$Q^1$: a carbocyclic group that may be substituted and may be condensed; and
$Q^2$: a heterocyclic group that may be substituted and may be condensed,
with the proviso that the case where —$X^A$-Q is —CONR$^1$—X—R$^2$ (wherein R¹ is hydrogen or lower alkyl,
X is a single bond; a heteroatom group selected from O, S, SO, SO₂, and NH; or lower alkylene or lower alkenylene that may be intervened by the heteroatom group, and
R² is optionally substituted aryl)
is excluded;
  R³ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino;
  R⁴ is hydrogen, optionally substituted lower alkyl (with the proviso that the substituent is not optionally substituted aryl), optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, SO₂, NRᵃ (wherein Rᵃ is hydrogen or lower alkyl), —N=, and =N—);
or a pharmaceutically acceptable salt thereof, or a solvate thereof.

5. A compound represented by the formula QI-B:

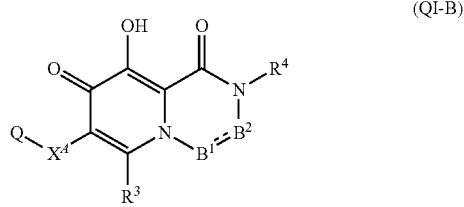

(QI-B)

wherein
  the broken line represents the presence or absence of a bond;
  B¹ is CR²⁰R²¹;
  B² is NR²² and R⁴ and R²² taken together form an optionally substituted heterocycle; or
  B¹ is NR²²;
  B² is CHR²¹ and R⁴ and R²¹ taken together form an optionally substituted heterocycle; or
  B¹ and B² are each independently C, CR²³, or N, and in this case, the B¹ and B² parts are taken together to form an optionally substituted heterocycle;
  R²⁰, R²¹, R²², and R²³ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, lower alkyl substituted with optionally substituted phosphoric acid residue (wherein the lower alkyl may be intervened by a heteroatom group selected from the group consisting of O, S, SO, SO₂, NR⁵ (wherein R⁵ is, independent of R⁴, selected from the same substituent group as R⁴), —N=, and =N—), hydroxy, optionally substituted amino, optionally substituted lower alkylcarbonyl, optionally substituted cycloalkyl carbonyl, optionally substituted cycloalkyl lower alkylcarbonyl, optionally substituted lower alkoxycarbonyl, optionally substituted aryl carbonyl, optionally substituted aryl lower alkylcarbonyl, optionally substituted aryloxycarbonyl, optionally substituted heterocyclylcarbonyl, optionally substituted heterocyclyl lower alkylcarbonyl, optionally substituted heterocyclyloxycarbonyl, optionally substituted aminocarbonyl, substituted (thio)urea, or substituted sulfonyl;
  Xᴬ is a group selected from the following group:
  Xᴬ¹: a single bond;
  Xᴬ²: a group selected from C=O and C=S;
  Xᴬ³: a heteroatom group selected from O, S, SO, SO₂, and NR¹' wherein R¹' is hydrogen or lower alkyl,
  Xᴬ⁴: a group formed by linking the same or different, two or more groups selected from Xᴬ² and Xᴬ³,
  Xᴬ⁵: a group selected from —N=N—, —C(R¹')=N—, or —N=C(R¹')— wherein R¹' is hydrogen or lower alkyl;
  Xᴬ⁶: optionally substituted lower alkylene or optionally substituted lower alkenylene,
  Xᴬ⁷: Xᴬ⁶ intervened by one or any two or more groups selected from Xᴬ², Xᴬ³, Xᴬ⁴, and Xᴬ⁵; and
  Xᴬ⁸: a spacer consisting of any combination of Xᴬ¹ to Xᴬ⁷;
  Q is a group selected from the following group:
  Q¹: a carbocyclic group that may be substituted and may be condensed; and
  Q²: a heterocyclic group that may be substituted and may be condensed,
  with the proviso that the case where —Xᴬ-Q is —CONR¹—X—R² (wherein
R¹ is hydrogen or lower alkyl,
X is a single bond; a heteroatom group selected from O, S, SO, SO₂, and NH; or lower alkylene or lower alkenylene that may be intervened by the heteroatom group, and
R² is optionally substituted aryl)
is excluded;
  R³ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocyclyloxy, or optionally substituted amino;

$R^4$ is hydrogen, optionally substituted lower alkyl (with the proviso that the substituent is not optionally substituted aryl), optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocyclyl lower alkyl, optionally substituted heterocyclyloxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened by a heteroatom group selected from the group consisting of CO, O, S, SO, $SO_2$, $NR^a$ (wherein $R^a$ is hydrogen or lower alkyl), —N=, and =N—);

or a pharmaceutically acceptable salt thereof, or a solvate thereof.

6. The compound according to any one of claims 1 and 2-5, or a pharmaceutically acceptable salt thereof, or a solvate thereof, wherein $X^A$ in —$X^A$-Q is —$CONR^{1'}$—, —$CONR^{1'}$—$X^{46}$—, or —$CONR^{1'}$—$X^{47}$— in which each symbol is defined the same as above.

7. The compound according to any one of claims 1 and 2-5, or a pharmaceutically acceptable salt thereof, or a solvate thereof, wherein Q is $Q^2$: a heterocyclic group that may be substituted and may be condensed.

8. The compound according to claim 7, or a pharmaceutically acceptable salt thereof, or a solvate thereof, wherein Q is a 5- to 7-membered heterocyclic group which may be substituted, may be condensed, and contains one to four heteroatoms that are one or the same or different, two or more heteroatoms selected from O, S and N atoms.

9. The compound according to any one of claims 1 and 2-5, or a pharmaceutically acceptable salt thereof, or a solvate thereof, wherein Q is $Q^1$: a carbocyclic group that may be substituted and may be condensed.

10. The compound according to any one of claims 1 and 2-5, or a pharmaceutically acceptable salt thereof, or a solvate thereof, wherein Q is cycloalkyl that may be substituted and may be condensed.

11. The compound according to any one of claims 1 and 2-5, or a pharmaceutically acceptable salt thereof, or a solvate thereof, wherein $X^A$ in —$X^A$-Q is —$CONR^{1'}$—, —$CONR^{1'}$—$X^{46}$—, or —$CONR^{1'}$—$X^{47}$— in which each symbol is defined the same as above; Q is $Q^2$: a heterocyclic group that may be substituted and may be condensed, or cycloalkyl that may be substituted and may be condensed.

12. The compound according to any one of claims 1 and 2-5, or a pharmaceutically acceptable salt thereof, or a solvate thereof, wherein $R^3$ is hydrogen.

13. The compound according to claim 2, or a pharmaceutically acceptable salt thereof, or a solvate thereof, wherein $R^3$, $R^{14}$, and $R^X$ are hydrogen; and the broken line represents the absence of a bond.

14. A pharmaceutical composition comprising a compound according to any of claims 1 and 2-12, or a pharmaceutically acceptable salt thereof, or a solvate thereof.

15. The pharmaceutical composition according to claim 14, which is an anti-HIV agent.

16. The pharmaceutical composition according to claim 14, which is an integrase inhibitor.

* * * * *